United States Patent [19]

Yoshikumi et al.

[11] 4,440,757

[45] * Apr. 3, 1984

[54] PHARMACEUTICAL COMPOSITION COMPRISING DERIVATIVE OF AMINOBENZOIC ACID FOR REGULATING PROSTAGLANDIN

[75] Inventors: Chikao Yoshikumi, Kunitachi; Yoshio Ohmura, Funabashi; Fumio Hirose, Tokyo; Masanori Ikuzawa, Tachikawa; Kenichi Matsunaga, Tokyo; Takayoshi Fujii, Tokyo; Minoru Ohhara, Tokyo; Takao Ando, Tokyo, all of Japan

[73] Assignee: Kureha Kagaku Kogyo Kabushiki Kaisha, Tokyo, Japan

[*] Notice: The portion of the term of this patent subsequent to Feb. 2, 1999 has been disclaimed.

[21] Appl. No.: 174,543

[22] Filed: Aug. 1, 1980

Related U.S. Application Data

[63] Continuation-in-part of Ser. No. 84,467, Oct. 12, 1979, Pat. No. 4,322,409, and a continuation-in-part of Ser. No. 81,190, Feb. 10, 1979, Pat. No. 4,322,408, and a continuation-in-part of Ser. No. 102,535, Dec. 11, 1979, Pat. No. 4,313,939, and a continuation-in-part of Ser. No. 102,224, Dec. 10, 1979, Pat. No. 4,315,921, said Ser. No. 84,467, said Ser. No. 81,190, is a continuation-in-part of Ser. No. 24,095, Mar. 26, 1979, abandoned, said Ser. No. 102,535, is a continuation-in-part of Ser. No. 39,218, May 15, 1979, abandoned, said Ser. No. 102,224, is a continuation-in-part of Ser. No. 39,282, May 15, 1979, abandoned.

[30] Foreign Application Priority Data

| Apr. 6, 1978 [JP] | Japan | 53-40594 |
| Apr. 10, 1978 [JP] | Japan | 53-42014 |
| Apr. 10, 1978 [JP] | Japan | 53-42015 |
| Apr. 11, 1978 [JP] | Japan | 53-42576 |
| May 26, 1978 [JP] | Japan | 53-63146 |
| Dec. 29, 1978 [JP] | Japan | 53-161385 |
| Dec. 29, 1978 [JP] | Japan | 53-161386 |
| Jul. 5, 1980 [JP] | Japan | 55-91113 |

[51] Int. Cl.$^3$ .............................................. A61K 31/70
[52] U.S. Cl. ...................................... 424/180; 536/22
[58] Field of Search ................... 424/180; 536/18, 22

[56] References Cited

U.S. PATENT DOCUMENTS 2,659,689  11/1953  Schreiber ............................ 536/18

OTHER PUBLICATIONS

Chemical Abstracts, vol. 48; 2001e, 2003a, 2003e, 1954.

Primary Examiner—Blondel Hazel
Attorney, Agent, or Firm—Wegner & Bretschneider

[57] ABSTRACT

A pharmaceutical composition for regulating prostagrandins, which comprises (a) a derivative of aminobenzoic acid, represented by the following general formula:

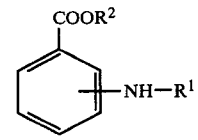

wherein $R^1$ denotes one member selected from the group consisting of the residual groups formed by removing OH at 1(alpha)-or 1(beta) position from arabinose, xylose, rhamnose, glucose, galactose, mannose and fructose, and $R^2$ is a hydrogen atom, an alkyl group of one to four carbon atoms or a pharmaceutically acceptable metal, and (b) a pharmaceutically acceptable carrier or diluent of (a) is disclosed.

8 Claims, 16 Drawing Figures

PHARMACEUTICAL COMPOSITION COMPRISING DERIVATIVE OF AMINOBENZOIC ACID FOR REGULATING PROSTAGLANDIN

CROSS-REFERENCE TO RELATED APPLICATIONS

This application is a continuation-in-part of each of the following copending applications: Ser. No. 84,467, filed Oct. 12, 1979 U.S. Pat. No. 4,322,409 Ser. No. 81,190, filed Feb. 10, 1979, U.S. Pat. No. 4,322,408; Ser. No. 102,535, filed Dec. 11, 1979, U.S. Pat. No. 4,313,938; and Ser. No. 102,224, filed Dec. 10, 1979, U.S. Pat. No. 4,315,921. Each of the four above applications is respectively itself a continuation-in-part of the following applications copending therewith: Ser. No. 24,092, filed Mar. 26, 1979 now abandoned; Ser. No. 24,095, filed Mar. 26, 1979 now abandoned; Ser. No. 39,218, filed May 15, 1979 now abandoned; and Ser. No. 39,282, filed May 15, 1979 now abandoned.

BACKGROUND OF THE INVENTION

The present invention concerns a pharmaceutical composition for use in regulating prostaglandins in mammalian living bodies, which comprises (a) as an active ingredient, a derivative of aminobenzoic acid represented by the following general formula:

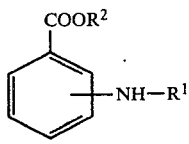

(1)

wherein $R^1$ denotes one member selected from the group consisting of the residual groups formed by removing OH at 1(alpha)- or 1 (beta) position from arabinose, xylose, rhamnose, glucose, galactose, mannose and fructose, and $R^2$ is a hydrogen atom, an alkyl group of one to four carbon atoms or a pharmaceutically acceptable metal and (b) a pharmaceutically acceptable carrier or diluent therefor.

A group of compounds generically called as prostaglandin (hereinafter referred to PG or PGs (the plural)) have come to be regarded as important recently, because of their various physiological functions in mammalian living bodies. However, since some of PGs have short half-lives or are not stable, there have been problems in utilizing PGs as pharmaceuticals.

There is a method for regulating PGs formed within the mammalian living bodies, for instance, the administration of aspirin (refer to Nature, No. 239: 33–34, 1972). However, aspirin is an inhibitor of cyclooxygenase which participates in the earlier stage of the metabolism of PGs, and accordingly, aspirin should be positioned as the blocker of all PGs. In other words, aspirin should be called as a regulator of the production of all PGs, and it has no activity of raising the production of a certain PG or certain PGs, and accordingly, there is naturally a limit in aspirin's activity as a regulator of PGs. In addition, aspirin has its side-effect of causing gastroenteric disorders in mammals, therefore, there has been a problem concerning the long term administration of aspirin.

The inventors of the present invention, after studying to find out a compound which is possible to regulate PGs without exhibiting side effects as far as possible, have found that a series of derivatives of aminobenzoic acid represented by the above-mentioned general formula (1) effectively regulate PGs, and have attained to the present invention.

The above-mentioned derivative of aminobenzoic acid for use as an active ingredient according to the present invention is a chemically and physically known compound. Inoue et al. disclosed the chemical synthesis of the above-mentioned compound (refer to J. Agr. Chem. Soc. Japan, Vol. 25, pp 59–63 and 291–293 (1951), and Chemical Abstracts Vol. 48, Columns 2001d and 2001i (1954)) and some physical properties of the compound (refer to J. Agr. Chem. Soc. Japan, Vol. 26, pp 329–331 (1952)), and Chemical Abstracts Vol. 48, Column 2003a (1954)).

However, in the above-mentioned literatures, nothing is disclosed concerning the physiological or pharmaceutical properties of the above-mentioned compound. Moreover, no report has been found hitherto found concerning the physiological and/or pharmacological properties of the compound represented by the general formula (1).

SUMMARY OF THE INVENTION

In an aspect of the invention, there is provided a pharmaceutical composition having effectiveness in regulating prostaglandins (PGs) in mammalian living bodies, based on the discovery of the new medical use of the chemical compounds represented by the above-mentioned general formula (1).

DETAILED DESCRIPTION OF THE INVENTION

Figure 1:
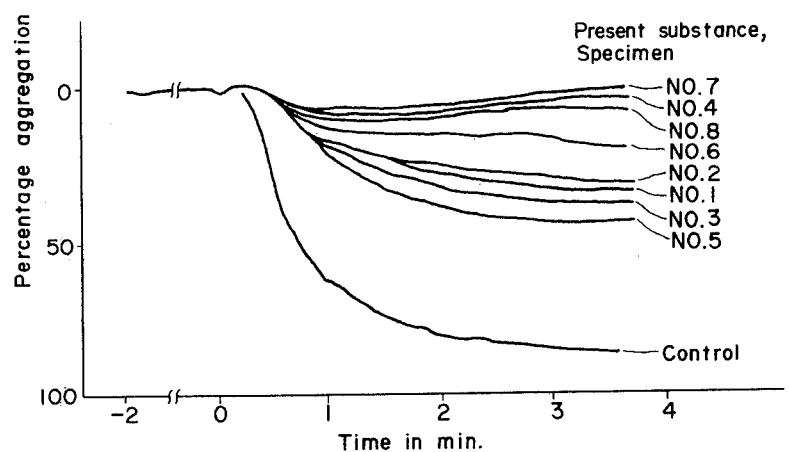
FIG. 1 shows the effect of the present substance on the aggregation of platelets by arachidonic acid.
Figure 2:
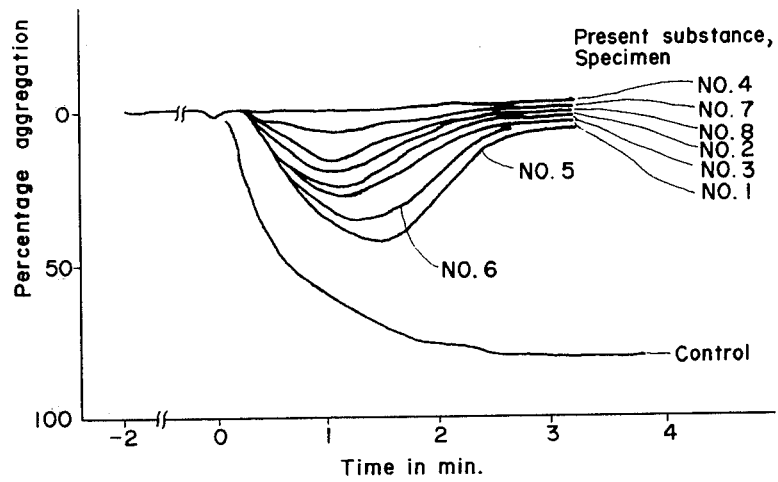
FIG. 2 shows the effect of the present substance on the aggregation of platelets by adenosine diphosphate (ADP)
Figure 3:
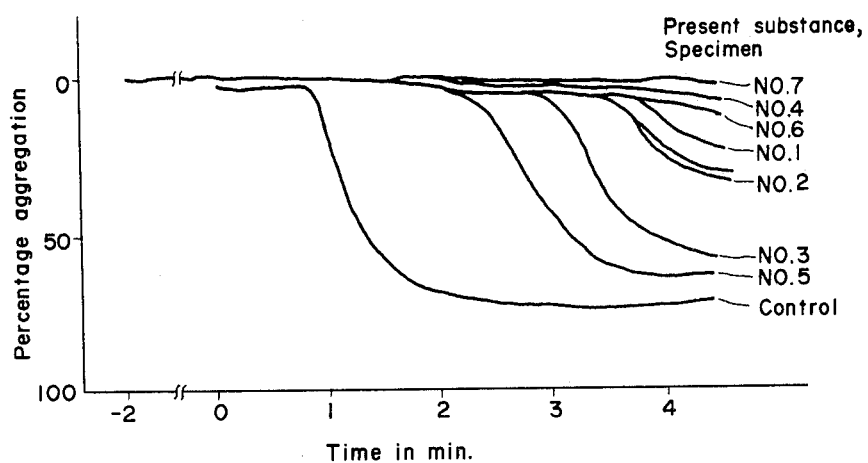
FIG. 3 shows the effect of the present substance on the aggregation of platelets by collagen.
Figure 4:
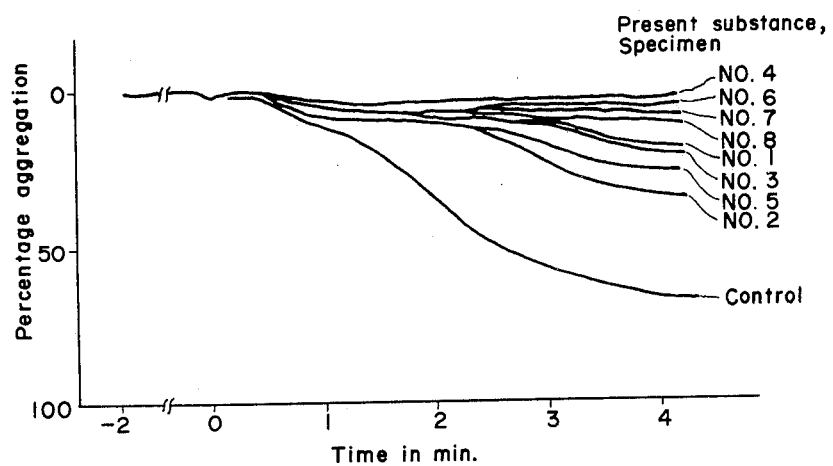
FIG. 4 shows the effect of the present substance on the aggregation platelets by epinephrine.
Figure 5:
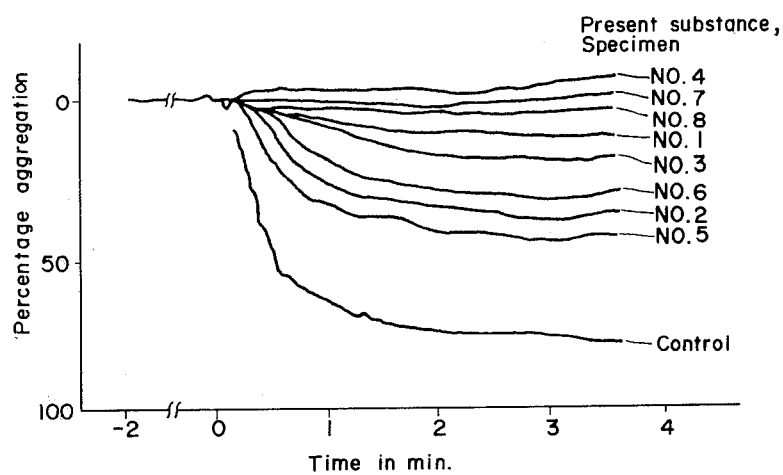
FIG. 5 shows the effect of the present substance on the aggregation of platelets by ristocetin.
Figure 6:
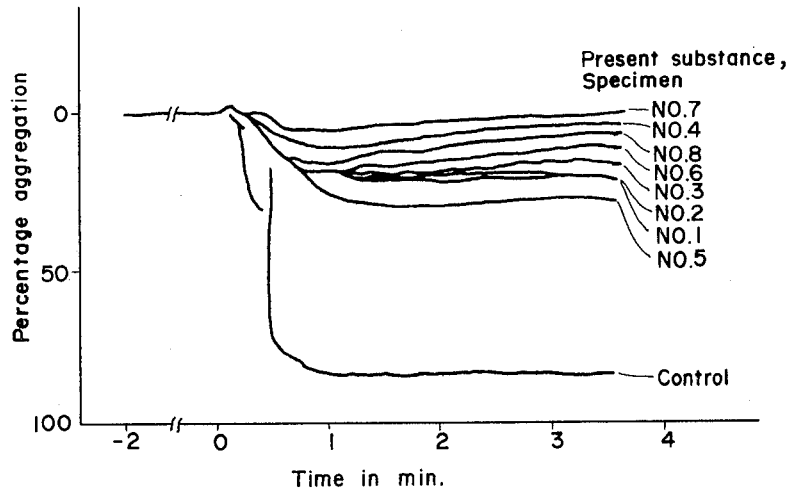
FIG. 6 shows the effect of the present substance on the aggregation of platelets by thrombin.

The active ingredient of the pharmaceutical composition according to the present invention (hereinafter referred to as the present substance) is a compound represented by the following formula (1):

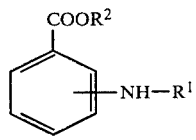

wherein $R^1$ denotes one member selected from the group consisting of the residual groups formed by removing OH at 1(alpha)- or 1(beta) position from arabinose, xylose, rhamnose, glucose, galactose, mannose and fructose, and $R^2$ is a hydrogen atom, an alkyl or one to four carbon atoms or a pharmaceutically acceptable metal.

Since the present substance, as will be explained later, is extremely low in acute oral toxicity, has no mutagenecity, does not affect the cellular and humoral immunity of the host and does not disturb the gastrointestinal bacterial flora because of the absence of antibacterial activity, it can be orally administered for long term without possibility or risk of causing mutagenesis and allergy to persons.

Accordingly, the substance of the present invention is highly safe as a pharmaceutical.

In the above-mentioned general formula (1) of the present substance, $R^1$ denotes, in short, a residue of a monosaccharide, and the monosaccharide may be either D-form or L-form, either alpha-anomer or beta-anomer or a mixture of the anomers. Accordingly, the present substance itself may be also either alpha-anomer or beta-anomer, or a mixture of the anomers.

In the above-mentioned general formula (1), $R^2$ is a hydrogen atom, a pharmaceutically acceptable metal such as Na, K, 1/2 Ca, 1/2 Mg, 1/3 Al, or an alkyl such as methyl, ethyl, propyl and butyl.

The method of preparation of the present substance is exemplified as follows:

A mixture of 5 g of p-aminobenzoic acid, 5 to 6 of a monosaccharide such as L-arabinose, D-xylose, L-rhamnose, D-glucose, D-galactose, D-mannose and D-fructose and 0.1 to 0.5 g of ammonium chloride, magnasium chloride, formic acid, acetic acid or hydrochloric acid was heated in 40 to 90 ml of 95 to 100% ethanol or pure methanol under a reflux condenser to induce condensation. After the reaction was over, the reactant was left at room temperature or in a cool place and the crystals separated out were collected by filtering the reactant solution. These crystals were washed with water, ethanol or ethyl ether, and then recrystallized from methanol, ethanol or an aqueous solution of methanol or ethanol.

In order to substitute the hydrogen atom of the carboxyl group of the thus prepared compound with a base, it is preferable to follow the known method. The compound, p-aminobenzoic acid -N-pyranoside, is dissolved in an aqueous ethanolic solution and an inorganic salt is added to the solution to effect the substitution.

The physical properties of some of the present substances (the active ingredient of the pharmaceutical composition of the present invention) prepared by the above-mentioned methods are shown in Table 1. The present substances shown in Table 1 are hereinafter referred to as Specimens Nos. 1 to 11.

TABLE 1

| | Physical Properties of the Active Ingredients | | | | |
|---|---|---|---|---|---|
| Specimen No. | Name of the present substance | Melting point (°C.) | Specific rotation $\|\alpha\|_D^{20}$ | Elementary analysis (%) C:H:N | Ultraviolet absorption Maximum (millimicron) |
| 1 | Sodium o-aminobenzoate-N—D-galactoside | 157–163 (decomp.) | −9 in water | 48.5:5.2:4.4 (48.6:5.0:4.4)* | 317, 248, 215 |
| 2 | Sodium o-aminobenzoate-N—L-rhamnoside | 152–162 (decomp.) | +54 in water | 51.0:5.4:4.9 (51.1:5.2:4.6) | 320, 249, 215 |
| 3 | Sodium m-aminobenzoate-N—D-mannoside | 130–145 | +5 (H$_2$O) | 48.5:5.0:4.2 (48.6:5.0:4.4) | 274 |
| 4 | Sodium p-aminobenzoate-N—D-mannoside | 185–196 (decomp.) | −2 in water | 46.1:5.5:4.0 (46.0:5.3:4.1) | 274 |
| 5 | Sodium p-aminobenzoate-N—D-glucoside | 145–160 | −55 in water | 45.8:5.2:4.3 (46.0:5.3:4.1) | 274 |
| 6 | Sodium p-aminobenzoate-N—D-galactoside | 150–162 | +10 in water | 46.0:5.6:4.1 (46.0:5.3:4.1) | 275 |
| 7 | Sodium p-aminobenzoate-N—D-xyloside | 149–158 | 0 in water | 49.3:4.9:4.8 (49.5:4.8:4.8) | 274 |
| 8 | Sodium p-aminobenzoate-N—L-rhamnoside | 173–178 (decomp.) | +80 in water | 51.0:5.1:4.8 (51.1:5.2:4.6) | 273 |
| 9 | Sodium p-aminobenzoate-N—D-fructoside | 180–205 | −4 in water | 48.8:4.9:4.3 (48.6:5.0:4.4) | 290 |
| 10 | Sodium p-aminobenzoate-N—L-arabinoside | 163–173 (decomp.) | −41 in water | 50.0:4.2:4.7 (49.8:4.2:4.8) | 274 |
| 11 | Methyl o-aminobenzoate-N—D-mannoside | 177–178 | −54 in ethanol | 49.1:6.1:4.3 (48.1:6.6:4.0) | 330, 251 |

Note:
*Parenthesized figures show the theoretical values of C, H and N (%).

(1) Melting point: determined by the use of micro melting point determination apparatus made by Yanagimoto Works, Japan.

(2) Specific rotation: determined by using direct-reading polarimeter Model OR-50 made by Yanagimoto Works, Japan, with a thickness of 50 mm of an aqueous ethanolic solution of the acidic active ingredient and an aqueous solution of the sodium salt of the acidic active ingredient.

(3) Molecular composition: Elementary analysis was carried out by using CHN-Coder Model MT-2 made by Yanagimoto Works, Japan.

(4) Ultraviolet absorption spectrum: by using self-recording spectrophotometer Model PS-3T made by Hitachi Works, Japan, on an aqueous ethanolic solution of the acidic active ingredient and on an aqueous solution of the sodium salt of the acidic active ingredient of the medicine.

The followings are the physiological properties of the present substances described in the order of (1) acute toxicity, (2) antimicrobial activity, (3) mutagenicity, (4) delayed-type intracutaneous reaction, (5) antibody-producing activity and (6) effect on the stomach.

(1) Acute oral toxicity:

The acute oral toxicity of the present substances were examined by using groups of ICR-JCL mouse and orally administering each of the representatives of present substances forcibly as an aqueous solution in distilled water or as an aqueous suspension also in distilled water at predetermined dosages, respectively. After observing the toxicological symptoms, if any, for 6 days, and recording the mortality until 7th day of the administration, $LD_{50}$ (acute oral) was calculated by the method of Litchfield-Wilcoxon, and autopsy was carried out on dead mice and live mice to obtain informations.

The results are shown in Table 2. As is seen in Table 2, $LD_{50}$ (acute oral) of the representatives of the present substance is very large showing that they are extremely low in toxicity.

TABLE 2

| | Acute oral toxicity of the representative substances: | |
|---|---|---|
| Specimen No. | Name of the present substance | $LD_{50}$ (g/kg) p.o. |
| 1. | Sodium o-aminobenzoate N—D-galactoside | 6.10 |
| 2. | Sodium o-aminobenzoate N—L-rhamnoside | 12.50 |
| 3. | Sodium m-aminobenzoate N—D-mannoside | >10 |
| 4. | Sodium p-aminobenzoate N—D-mannoside | >10 |
| 5. | Sodium p-aminobenzoate N—D-glucoside | >15 |
| 6. | Sodium p-aminobenzoate N—D-galactoside | 14.55 |
| 7. | Sodium p-aminobenzoate N—D-xyloside | 11.75 |
| 8. | Sodium p-aminobenzoate N—L-rhamnoside | 12.80 |
| 9. | Sodium p-aminobenzoate N—D-fructoside | >10 |
| 10. | Sodium p-aminobenzoate N—L-arabinoside | 10.80 |
| 11. | Methyl o-aminobenzoate N—D-mannoside | >7.5 |

In addition, no abnormal findings was obtained on autopsy on dead animals and live animals.

(2) Anti-microbial activity:

The present substance was dissolved in distilled water at a series of two fold dilution system. These diluted solutions were mixed with agar medium in 9 times by volume and the mixture was poured into a petridish. Heartinfusion agar medium was used for bacteria, and Sabouraud's agar medium was used for fungi. After streaking with the pre-culture, the inoculated plates were incubated at 37° C. for 20 to 24 hours for bacteria and at 25° C. for 3 to 7 days for fungi, and then the growth was examined. The following microorganisms were used for assessing the antimicrobial activity of the present substance:

*Pseudomonas aeruginosa* IAM 1514
*Escherichia coli* IFO 12734
*Staphylococcus aureus* 209 P
Bacillus subtilis IAM 1069
*Saccharomyces cerevisiae* IAM 4207
*Candida albicans* ATCC 752
*Trichophyton mentagrophytes* IFO 6124
*Aspergillus niger* IAM 3001

As the result of the above-mentioned tests, it was found that none of the tested active ingredients showed growth inhibition of all the microorganisms at a concentration of 1 mg/ml.

(3) Mutagenicity:

As the first stage, the present substances were tested by rec-assay (i), and as the second stage, they were tested by reversion assay (ii).

(i) A strain of *Bacillus subtilis* M 45, a defectant of recombination repair, and a wild strain of *Bacillus subtilis* H 17 keeping recombination repair activity were inoculated to make their own streaks not crossed at the start on a B-2 agar culture plate (made by dissolving 10 g of meat extract, 10 g of polypeptone, 5 g of sodium chloride and 15 g of agar in 1000 ml of distilled water at pH 7.0). Then, a paper disc of 8 mm in diameter, which absorbed 0.04 ml of an aqueous solution of the present substance in sterilized water was put on the surface of the agar plate so as to cover the starting point of the above-mentioned streaks of bacterial culture. The inoculated B-2 agar plate was kept at 37° C. for a night and the length of growth-inhibited region was measured. Kanamycin was used as the negative control and Mitomycin C was used as the positive control. The results of the rec-assay are shown in Table 3.

(ii) The strains TA 98 and TA 100 (both are histidine requiring) of *Salmonella typhimurium* were used in the reversion assay.

Into 2 ml of a soft agar culture medium (the medium itself contains 6 g of sodium chloride and 6 g of agar in 1000 ml of distilled water) to which one tenth by volume of an aqueous solution of 0.5 mM of biotin and 0.5 mM of histidine had been added, 0.1 ml of the bacterial suspension and 0.1 ml of an aqueous solution of the present substance were admixed and the mixture was layered on the minimum agar culture medium. After 2 days of incubation at 37° C., the number of revertant colonies was counted. Furylfuramide (AF-2) was used as the positive control. The results of the reversion assay are shown in Table 4.

As is seen in Table 3, the present substances showed a weak mutagenicity only at a high concentration of 5000 microgram/disk. And as is seen in Table 4, the rate of occurrence of mutation by the present substance did not shown any difference form that in the control to which no substance was added, even at a high concentration of 5000 microgram/plate. These findings demonstrate that the present substance is safe in view of mutagenicity.

TABLE 3

Result of rec-assay

| Specimen No. | Name of the present substance | Concentration (μg/disk) | Length of inhibition M 45 (mm) | Length of inhibition H 17 (mm) | growthzone *difference (mm) |
|---|---|---|---|---|---|
| 1. | Sodium o-aminobenzoate-N—D-galactoside | 500 | 0 | 0 | 0 |
|  |  | 5,000 | 6 | 1 | 5 |
| 2. | Sodium o-aminobenzoate-N—L-rhamnoside | 500 | 0 | 0 | 0 |
|  |  | 5,000 | 6 | 2 | 4 |
| 3. | Sodium m-aminobenzoate-N—D-mannoside | 500 | 0 | 0 | 0 |
|  |  | 5,000 | 7 | 1 | 6 |
| 4. | Sodium p-aminobenzoate-N—D-mannoside | 500 | 0 | 0 | 0 |
|  |  | 5,000 | 0 | 0 | 0 |
| 5. | Sodium p-aminobenzoate-N—D-glucoside | 500 | 0 | 0 | 0 |
|  |  | 5,000 | 0 | 0 | 0 |
| 6. | Sodium p-aminobenzoate-N—D-galactoside | 500 | 0 | 0 | 0 |
|  |  | 5,000 | 0 | 0 | 0 |
| 7. | Sodium p-aminobenzoate-N—D-xyloside | 500 | 0 | 0 | 0 |
|  |  | 5,000 | 0 | 0 | 0 |
| 8. | Sodium p-aminobenzoate-N—L-rhamnoside | 500 | 0 | 0 | 0 |
|  |  | 5,000 | 0 | 0 | 0 |
| 9. | Sodium p-aminobenzoate-N—D-fructoside | 500 | 0 | 0 | 0 |
|  |  | 5,000 | 0 | 0 | 0 |
| 10. | Sodium p-aminobenzoate-N—L-arabinoside | 500 | 0 | 0 | 0 |
|  |  | 5,000 | 0 | 0 | 0 |
| 11. | Methyl o-aminobenzoate-N—D-mannoside | 500 | 0 | 0 | 0 |
|  |  | 5,000 | 7 | 3 | 4 |
|  | Kanamycin | 10 | 5 | 4 | 1 |
|  | Mitomycin C | 0.05 | 12 | 2 | 10 |

Note:
*Difference = length of inhibition zone of M 45 minus length of inhibition zone of H 17.

TABLE 4

Results of Reversion assay

| Specimen No. | Name of the present substance | Concentration (μg/plate) | Number of revertant colonies (number per plate) TA 100 | TA 98 |
|---|---|---|---|---|
| 1. | Sodium o-aminobenzoate-N—D-galactoside | 5,000 | 151 | 6 |
| 2. | Sodium o-aminobenzoate-N—L-rhamnoside | 5,000 | 61 | 9 |
| 3. | Sodium m-aminobenzoate-N—D-mannoside | 5,000 | 90 | 6 |
| 4. | Sodium p-aminobenzoate-N—D-mannoside | 5,000 | 138 | 5 |
| 5. | Sodium p-aminobenzoate-N—D-glucoside | 5,000 | 104 | 11 |
| 6. | Sodium p-aminobenzoate-N—D-galactoside | 5,000 | 51 | 7 |
| 7. | Sodium p-aminobenzoate-N—D-xyloside | 5,000 | 58 | 4 |
| 8. | Sodium p-aminobenzoate-N—L-rhamnoside | 5,000 | 73 | 4 |
| 9. | Sodium p-aminobenzoate-N—D-fructoside | 5,000 | 95 | 5 |
| 10. | Sodium p-aminobenzoate-N—L-arabinoside | 5,000 | 51 | 3 |
| 11. | Methyl o-aminobenzoate-N—D-mannoside | 5,000 | 95 | 8 |
|  | Furylfuramide | 0.1 | 911 | 167 |
|  | Control (nothing added) | — | 149 | 13 |

(4) Delayed-type intracutaneous reaction:

In order to know the effects of the present substances on cellular immunity, the foot pad reaction test was carried out using ICR-JCL mice as experimental animals and erythrocytes of sheep as an antigen.

A mouse was primary-sensitized by injecting 0.2 ml of an aqueous 10% suspension of sheep erythrocytes in physiological saline solution from the caudal vein and after 7 days of the first sensitization, 0.05 ml of an aqueous 40% suspension of sheep erythrocytes in physiological saline solution was injected in the foot pad for the second sensitization. The thickness of the foot pad was determined on the next day. The administration of the present substance was carried out at the dosage of 250 mg/kg/day once a day for consecutive 5 days centering around the day when the first sensitization was carried out.

As the result, the increment of the thickness of the foot pad of the mouse administered with the present substance showed no significant difference as compared to the increment in the group of mouse not administered with the active ingredient.

(5) Antibody-producing activity:

In order to know the effects of the present substances on humoral immunity, the hemagglutination test was carried out using ICR-JCL mice sensitized with sheep erythrocytes.

A mouse was sensitized by injecting 0.2 ml of an aqueous 10% suspension of sheep erythrocytes in physiological saline solution from the caudal vein and after 7 days of sensitization the mouse blood was sampled for the hemagglutination test of determination of the antibody-producing activity. The present substance was administered for consecutive 5 days centering around the day of sensitization, intraperitoneally at the dosage of 250 mg/kg/day.

As the result, there was no significant difference in agglutination titer between the group administered with the present substance and the control group.

(6) Effect of the present substance on the stomach:

Five grams of the present substance (each of Specimens Nos. 1, 2, 3, 4, 5, 6, 7, 8, 9, 10 and 11) and of aspirin were respectively administered to each Beagle of body weight of 9 to 12 kg as an aqueous suspension in distilled water of adjusted pH of 3, and after 90 min of the administration, the state of hemorrhage in the dog's stomach was examined. As the result, hemorrhage in the stomach was observed only on the dogs administered with aspirin, however, no hemorrhage in the stomach was found on the dogs respectively administered with each of Specimens Nos. 1 to 11.

The following description is the summary of the pharmaceutical specificities of the present substances, the more detailed description appearing in Examples:

(1) Regulation of prostaglandin

The present substance concerns the regulation of PGs such as PGA, PGB, PGC, PGD, PGE, PGF, PGG, PGH, PGI, TXA, and TXB and the metabolic products of them. In addition, the present substance not only regulates any one of the above-mentioned PGs but also regulates several kinds of PGs.

The regulating function of the present substance on the production of PGs and their metabolites are shown by the following facts:

(a) Supression of aggregation of the platelets

It has been known that the aggregation of the paltelets is mainly induced by $PGG_2$, $PGH_2$ and $TXA_2$, and it has been confirmed that the present substance has a function of suppressing the aggregation of the platelets (refer to Examples 2 and 5).

(b) Raising of cyclic adenosine monophosphate

It has been known that cyclic adenosine monophosphate (cyclic AMP) is closely related to PGs, particularly to PGD, PGE and PGI, and the present substance showed a function of raising the level of cyclic AMP in the platelets and the cells in culture (refer to Examples 3, 6 and 8).

(c) Suppression of the production of malondialdehyde

It has been confirmed that the present substance has an inhibiting action on the production of malondialdehyde (MDA) in the platelets, MDA having been known as a metabolic product of PGs (refer to Example 4).

(d) Acceleration of the production of $PGI_2$

It has been confirmed that the present substance acts acceleratively on the production of $PGI_2$ in the cells cultured in vitro (refer to Example 7).

(e) Pertaining to the production of some PGs

According to the experimental results on the metabolism of PGs in vitro using arachidonic acid as a starting material, it has been shown that the present substance relates to the production of $PGD_2$, $PGE_2$, 6-keto-$PGF_{1-\alpha}$ and $PGF_{2-\alpha}$ (refer to Example 1).

(f) Effect on the biosynthesis of PGE and $PGF_{2-\alpha}$

It has been shown in a in vitro culture experiment of cells, that the substance of the present invention has an effect on the bio-synthesis of PGE and $PGF_{2-\alpha}$ (refer to Examples 9 and 10).

(g) Inhibition of proliferation of tumour-cells

The examination of the proliferation of tumour-cells and the level of intra-tumour cell-PGE on tumour-bearing experimental animals administered with the substance of the present invention confirmed the inhibition of the proliferation of the tumour cells and also the raising of the level of PGE in tumour cells of the animals administered with the present substance (refer to Examples 11, 12, 13 and 14).

(h) Fortifying effect on the transfer of pigment

In an experiment in which the present substance was administered to tumour-bearing experimental animals and the degree of transfer of a dye-staff into the tumour-tissue of the animal was examined, a fortifying effect on the transfer of the exogenous dye-staff was confirmed suggesting the blood-vessel dilating effect of the present substance (refer to Example 15).

(i) Inhibition on metastasis of tumours

In an experiment in which the present substance was administered to experimental animals before and after the transplantation of tumour cells to the animals, an effect of inhibiting the metastasis of the transplanted tumour cells was recognized (refer to Example 16).

(j) Reduction of the level of 6-keto-$PGF_{1-\alpha}$

In tumour-bearing animals, it has been observed that the level of 6-keto-$PGF_{1-\alpha}$ in their plasma is remarkably raised as compared to that of non-tumour-bearing animals, however, it has been confirmed that the once raised level is reduced to the normal level by the administration of the present substance (refer to Example 17).

In general, PGs have been found in several organs of whole body, and they have their close relationships to the functions of the organs. Furthermore, it has been known that the physiological and pharmacological functions of PGs cover an extremely broad region. That is, PGs act mainly on the dilation and contraction of blood vessels as their pharmacological action on circulation system, PGE and PGI being stronger in dilating, and TXA, on the contrary, contracting the artery. These functions cause the raise or the reduction of blood pressure as the results, and mean the remedial function on the stenocardia and the arrhythmia.

Although the excessive proceeding of an action of aggregating the platelets causes the arteriosclerosis, the cerebral infarct, the myocardial infarction and the cerebral apoplexy, PGs have strong effects on the platelets. That is, PGD, PGE and PGI have an antagonistic function against the action of aggregating platelets, and $TXA_2$, $PGG_2$, $PGH_2$ and $PGE_2$ have an inducing or acclerating action on the aggregation. Accordingly, it will be clearly understood that the treatments and the prevention of the above-mentioned diseases would be made possible by an appropriate adjustment of PGs.

Moreover, in the diabetes, it has been reported that the production of $PGI_2$ in the vascular system of the patient suffering from diabetes is limited, or the content of PGE and $PGF_2$ is high, and thus the relationship between this disease and PGs has been gradually elucidated.

The functions of PGs in the respiratory system has also been studied and it is known that PGE reduces the airway resistance. The function is to suggest the function of PGE in anti-asthma, acceleration of respiration, anti-coughing and anti-expectoration.

On the other hand, as a function concerning immunity, the suppressing action on the release of the slow-reacting substance of anaphlaxis is recognized in $PGI_2$ and its metabolite, and also PGs have anti-allergic action, anti-anaphlaxis action, and it is easily presumable that PGs will be effective in treating various diseases due to auto-immunization, especially the intractable diseases represented by rheumatism.

It is well known that the now commercialized anti-inflammatory drug, indomethacin, relates to cyclooxygenase in the metabolic route of PGs and that several kinds of PGs concern the inflammatory action. In short, it will show that an anti-inflammatory effect is expected by the regulation of the metabolism of PGs.

On the other hand, PGs show a strong effect on the digestive system. That is, PGE and PGI suppress the secretion of the gastric juice, and it is said that as a result, they exhibit the anti-ulcer action. It is reported that particularly, the action is strong in PGI.

Concerning the kidney, it is reported that $PGI_2$ mainly shows a diuretic action. Among the commercialized antihypertensive agents, the position occupied by the diuretics is still important, and so the increased production of $PGI_2$ means its value as a diuretic and an antihypertensive agent.

The pharmacological action of PGs on the genital system is also well known, and PGs concern the facilitating action of uterine movement and uterine tension or inversely the suppressing action of uterine tension. These functions are the base of evaluation of PGs as an accelerating agent for delivery, a contraceptive and an agent for interrupting pregnancy.

Furthermore, an action of PGs as a psychonerval drug is under consideration. In the cerebral cells, a large amount of PGD is distributed, and now a relationship between the epilepsy and PGD is watched with keen interest.

It has been known that the peroxidation of lipid is accelerated by aging and arteriosclerosis, and that as a result, the activity of PGI-synthetic enzyme is suppressed. In addition, it is also reported that this PGI has a stabilizing action on the lysosome membrane. These facts show the value of PGI as an anti-peroxidized lipid agent and lead to the possibility of preventing the radiation disturbance and the aging.

Recently, PGs have been given attention in connection to cancers. Particularly, several studies have been carried out on PGD, PGE and PGI in the above-mentioned field, and it has been elucidated that these PGs concern the suppressing effect on the proliferation of cancer cells, the normalization of the cancer cells, the metastasis of cancer, etc. These facts are said to suggest the possibility of suppressing the proliferation of cancer and preventing the metastasis of cancer.

As has been described, the pharmacological functions of PGs cover various fields with various modes, and so it is no exaggeration to say that PGs concern all the diseases in some connection. Accordingly, the fact that the present substance regulates PGs gives us an expectation that PGs are useful in preventing and treating the above-mentioned diseases.

For instance, as for its anti-tumour function, as has been described before, an anti-tumour activity against L-cells is recognized in PGE [D. R. Thomas et al., Experimental Cell Research 84, 40–46 (1974)], and it has been recognized that the increase and decrease of PGD relates to the metastasis and the proliferation of tumours [F. A. Fitzpatrik et al., Proc. Natl. Acad. Sci., USA, 76 (4), 1765–1769 (1979)] and that PGI acts suppressively on the proliferation of tumours. However, these information only show that each prostaglandin has an anti-tumour activity as one of its physiological activities. On the other hand, as will be shown in Example 1, it has been elucidated by the inventor that the present substance has a function of changing the amount of both PGD and PGE in cells, that is, a function of regulating PGs which differs from each other in the same cell. Moreover, as is shown in another Example, it is clear that the present substance acts on TXA and PGI suppressively or acceleratively, and this fact clearly shows that the present substance not only changes a single prostaglandin but also changes various PGs simultaneously.

Such a substance changing many kinds of prostaglandins at the same time has never been recognized hitherto, and such a property may be said to be specific to the present substance.

Now, the formulation of the active ingredient to make the pharmaceutical composition of the present invention is described below.

In the case where the pharmaceutical composition is used as an PGs-regulating agent, it is able to use the pharmaceutical composition in the form which is convenient to obtain the effectiveness according to the kinds and the symptoms of the disease, and moreover, the active ingredient may be used as itself or may be used as mixtures combined with any diluent allowable in pharmaceutical process and with other medicines.

The pharmaceutical composition of the present invention is administered orally or parenterally and accordingly, the pharmaceutical composition of the present invention may take any form optionally for the oral or parenteral administration.

The pharmaceutical composition of the present invention may be offered as a form of unit administration. The form of the pharmaceutical composition of the present invention may be powder, granule, tablet, sugar-coated tablet, capsulated one, suppository, suspension, solution, emulsifiable concentrate, ampouled one, injection, etc. As a diluent, any one of solids, liquids and semisolids may be utilized, for instance, excipients, binders, wetting agents, disintegrating agents, surfactants, demulcents, dispersing agents, buffering agents, perfumes, preservatives, dissolution aids and solvents. Moreover, one or more than one of these adjuvants may be used in combination or in mixtures.

The pharmaceutical composition of the present invention may be formulated by any known method, and the amount of the active ingredient (the present substance) contained in the composition (preparation) is generally from 0.01% to 100% by weight.

The pharmaceutical composition of the present invention may be administered orally or parenterally to human or animals, however, it is preferably administered orally. Sublingual administration is included in oral administration. Parenteral administration includes subcutaneous-, intramuscular- and intravenous injection and the injection by drop method.

The dose of the pharmaceutical composition of the present invention depends upon the age, the personal difference and the state of disease, and whether the object is human or animal and accordingly, an extraordinal amount may be administered than the following dose: Generally, for human, the oral dose is 0.1–1000 mg/kg body weight/day, preferably 1–500 mg/kg/day and the parenteral dose is 0.01–200 mg/kg/day, preferably 0.1–100 mg/kg/day divided into 1–4 parts, one part being administered in one time.

The followings are the more detailed explanation of the formulation, the production and the physiological activities of the pharmaceutical composition of the present invention in examples.

EXAMPLE OF FORMULATION 1: (part means part by weight, hereinafter)

The following components were uniformly mixed, and the mixture was pulverized or finely granulated to be a powdery formulation of less than 350 in mean size:

| (1) Sodium p-aminobenzoate N—D-galactoside | 10 parts |
|---|---|
| (2) Heavy magnesium oxide | 15 parts |
| (3) Galactose | 75 parts |

The thus prepared formulation is used as it is, or after being capsulated.

EXAMPLE OF FORMULATION 2

The following components were uniformly mixed, pulverized and processed to wet granules. They are dried and sifted to be granules of 177 to 1410μ in size:

| (1) Sodium p-aminobenzoate N—D-xyloside | 45 parts, |
|---|---|
| (2) Starch | 15 parts, |
| (3) Galactose | 16 parts, |
| (4) Crystalline cellulose | 21 parts, |
| (5) Polyvinyl alcohol | 3 parts, and |
| (6) Water used for processing to prepare the wet granule | 30 parts. |

EXAMPLE OF FORMULATION 3

Instead of using sodium p-aminobenzoate N-D-xyloside in Example of formulation 2, by using sodium o-aminobenzoate N-L-rhamnoside, granular formulation was prepared as in Example of formulation 2. To 96 parts of the thus prepared granular formulation, 4 parts of calcium stearate were added and the mixture was compression-molded to be tablets of 10 mm in diameter.

EXAMPLE OF FORMULATION 4

To 90 parts of granular formulation prepared in Example of formulation 2, 10 parts of crystalline cellulose and 3 parts of calcium stearate were added, and the thus prepared mixture was compression-molded to be tablets of 3 mm in diameter. The thus prepared tablets were coated by a mixed suspension comprising syrup-gelatin and precipitated calcium carbonate to be sugar coated tablets.

EXAMPLE OF FORMULATION 5

The following components were mixed well while warming, and the mixture was ampouled and sterilized to be injection.

| (1) Sodium m-aminobenzoate N—L-rhamnoside | 0.6 part, |
|---|---|
| (2) A non-ionic surfactant | 2.4 parts and |
| (3) An aqueous physiological saline solution | 97 parts. |

EXAMPLE 1

Effect of the present substance on PGs metabolism of arachidonic acid taken into lymphocytes.

After adjusting the lymphocytes taken from the spleen of a BALB/C mouse to a concentration of $1 \times 10^7$ cells/ml, 2 μCi of $^3$H-arachidonic acid was added and the mixture was incubated at a temperature of 37° C. for 90 min. The incubated lymphocytes were washed three times with the culture medium. After again ajusting the cells to a concentration of $1 \times 10^7$ cells per ml, the culture was poured into four siliconized test tubes in an amount of 2 ml/tube. Two test tubes were used as control, and into each of the remaining two test tubes, 500 μg of the present substance, in this Example, Specimen No. 7 was added, and then the four test tubes were incubated at 37° C. for 60 min. After incubation, the test tubes were centrifuged at 0° C. for 5 min. at 1,200 rpm.

The thus obtained pellets of cells were taken into a vial containing 2 ml of the culture medium and after adding 5 ml of petroleum ether, the vial was shaken and the ether layer was removed, the remaining aqueous layer being adjusted to pH of 3.5 by aqueous 0.5 N hydrochloric acid solution.

The aqueous acidic solution was extracted three times with each 5 ml of ether, and the ether extract was dried to solid. The solid material was subjected to esterification by a solution of diazomethane. The esterified reaction mixture was subjected to thin-layer chromatography and was developed with a 90:50:20:100 (by volume) mixed solvent of ethyl acetate:iso-octane:acetic acid:water. The identification of the thus appeared spots on the chromatogram was carried out by using the following authentic specimens of $PGD_2$, $PGE_2$, $PGF_{2-\alpha}$ and 6-keto-$PGF_{1-\alpha}$. The silicagel layer of the separated chlomatogram was scraped out and dissolved into a liquid for the liquid scintillator to be counted. From the change of the counts the change of PGS was determined. The results are shown in Table 5.

TABLE 5

| | Change of Prostaglandins in Cell Culture in vitro | | | |
|---|---|---|---|---|
| | PGs | | | |
| Amount[1] | 6-keto-$PGF_{1-\alpha}$ | $PGF_{2-\alpha}$ | $PGE_2$ | $PGD_2$ |
| 0 | —[2] | — | — | — |
| 500 | ±[3] | ± | +[4] | + |

Notes:
[1]Amount of addition of the present substance, Specimen No. 7 (g/ml),
[2]no change was observed,
[3]change was slightly observed,
[4]change was clearly observed.

Similar results were obtained in the cases where Specimens Nos. 1 to 6 and 8 to 10 were respectively used at an amount of 500 μg/ml. These results show that the respective substances of the present invention regulate the metabolism of PGs even in in vitro test.

EXAMPLE 2

The action of the present substance on aggregation of platelets:

Since it has been elucidated that the aggregation of platelets is mainly induced by $PGG_2$, $PGH_2$ and $TXA_2$ all of which are series of PGs, the action of the present substance on aggregation of the platelets was examined as follows:

As the anti-coagulant, an aqueous solution of citrate for the determination of erythrocyte sedimentation was used, and to one part of the citrate solution nine parts of the human blood newly collected was added. The mixture was centrifuged for 6 min at 400XG, and the supernatant layer was used for preparing the human platelet rich plasma (PRP). The remainder was further centrifuged for 20 min at 700XG, and the supernatant was kept as the platelet poor plasma (PPP). The change of transmittance of PRP was measured in an agrigometer (Type PAP-3, manufactured by Biodata Co.) to determine the degree of aggregation of the platelets, the aggregation being caused by addition of an aggultinating agent.

The aggultinating agents used herein were arachidonic acid (1.64 mmol), adenoisine diphosphate (50

μmol), collagen (0.26 mg/ml), epinephrine (0.11 mmol), ristocetin (2.0 mg/ml) and thrombin (0.5 U per ml). Each of the agents was added to PRP after 2 min of the addition of one of the present substances (Specimens Nos. 1 to 8).

The results are shown in FIGS. 1 to 6. As is seen in Figs., every substance of the present invention tested herein showed an inhibiting effect against the aggregation of the platelets caused by every aggulutinating agent. The abovementioned phenomenon shows that every one of the present substances regulates the production of PGs, particularly that of $PGG_2$, $PGH_2$ and $TXA_2$.

EXAMPLE 3

Action of the present substance on the level of cyclic adenosine monophosphate (cyclic AMP)

Cyclic AMP is known to closely relate to PGs other than that it is known as an intracellular messenger, and the relationship is closer to PGD, PGE and PGI. Accordingly, in the present Example, the influence of the present substance on cyclic AMP in the cell of platelet was examined as follows:

PRP (platelet rich plasma) was prepared by the pre-determined method and it was centrifugated for 20 min at 700XG to obtain a supernatant liquid named PPP (platelet poor plasma). The precipitate was re-floated in ⅓ times by volume of PPP to prepare 3 times concentrated PRP.

Figure 7:
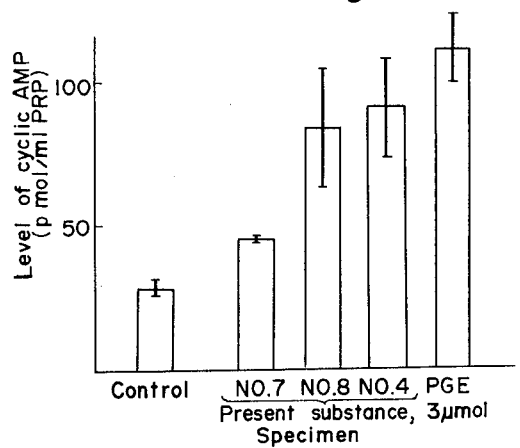
FIG. 7 shows the effect of the present substance on the level of cyclic adenosine monophosphate (cyclic AMP) in the platelet.

In the thus prepared concentrated PRP, each aqueous solution of the present substances of a pre-determined concentration (in this case, Specimens Nos. 4, 7 and 8) and an aqueous physiological saline solution, and the mixture was incubated at room temperature for 5 min. Then, the procedures of boiling, homogenating and centrifugating were carried out in this order, and 50 μl of the supernatant liquid was used for measuring cyclic AMP. The measurement was carried out following the method of Gilman. As a positive control, $PGE_1$ was used. The results are shown in FIG. 7. As is seen in FIG. 7, an action of raising the level of intra-platelet cellular cyclic AMP is shown in the present substance, and from this fact it is presumed that the present substance affects the metabolism of PGs.

EXAMPLE 4

Figure 8:
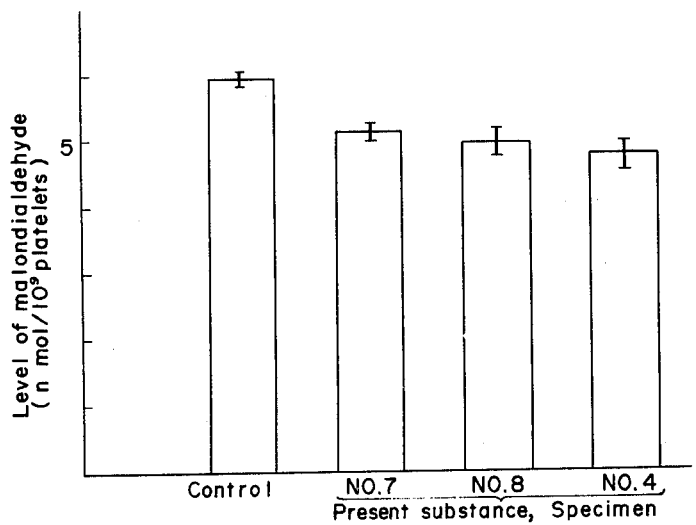
FIG. 8 shows the effect of the present substance on the production of malondialdehyde (MDA) in the platelet.

Action of the present substance on the level of malondialdehyde (MDA) of platelet:

PRP collected from human blood was centrifugated and washed to be "washed platelets". After adding one of the present substances (Specimens Nos. 4, 7 and 8) to the washed platelets, Caionophore A-23187 was further added to them and the mixture was incubated for 5 minutes at 37° C. Then, thiobarbituric acid was added to the incubated mixture, as a colour developer, and the mixture was extracted with a solvent mixture of methanol and butanol. The absorption at 535 nm was colorimetrically read to determine the amount of malondialdehyde (MDA). The results are shown in FIG. 8. The present substance suppressed the production of MDA. From this fact also, the participation of the present substance in the metabolism of PGs is presumable.

EXAMPLE 5

The effect of indomethacin on the hypotensive action of the present substance:

It is known that PGs are produced from arachidonic acid, and cyclooxygenase participates in the conversion of arachidonic acid to $PGG_2$, that indomethacin inactivates the above-mentioned cyclooxygenase and further that the metabolism of PGs is completely stopped by the administration of indomethacin.

Accordingly, the transition of blood pressure of the spontaneously hypertensive (SHR) male rats 30 to 40 weeks after birth was compared in both cases (1) where only the present substance was administered at a rate of 100 mg/kg and (2) where indomethacin was administered 2 times at a rate of 2.5 mg/kg/time before and after the administration of the present substance. The present substance, Specimen No. 7, was dissolved into distilled water or dispersed in an aqueous 2% solution of carboxymethylcellulose, and forcibly administered orally. Indomethacin was dispersed in an aqueous 2% solution of carboxymethylcellulose, and the dispersion was also forcibly administered orally, one hour before and after the administration of the present substance.

Figure 9:
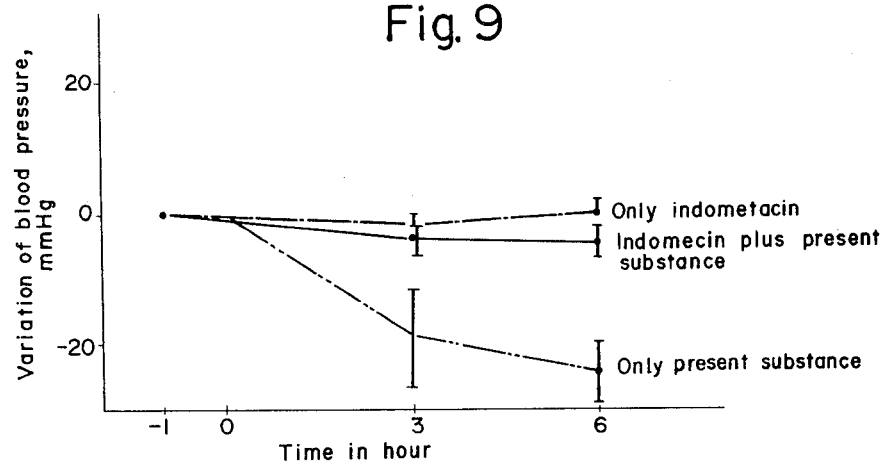
FIG. 9 shows the effect of indomethacin on the hypotensive action of the present substance.

The results are shown in FIG. 9. The hypotensive effect of the present substance disappeared in the case where indomethacin was administered before and after the administration of the present substance. In consideration that indomethacin is an inhibitor of the metabolism of prostaglandin, the effectiveness of the present substance in reducing the blood pressure is attributable to its close relationship to prostaglandin.

EXAMPLE 6

Figure 10:
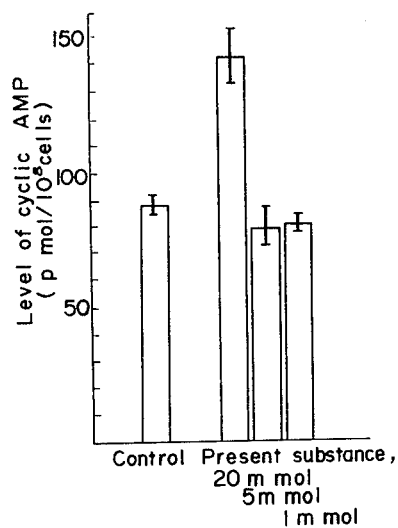
FIG. 10 shows the effect of the present substance on the level of cyclic AMP in cancer cells.

The action of the present substance on the level of cyclic AMP in the tumour cell of sarcoma 180:

The present substance was added to 100 μl of the ascites-type tumour taken from the abdominal cavity of sarcoma 180-bearing mice to be a predetermined concentration, in this case, Specimen No. 7, and the mixture was incubated at room temperature for 5 min. After incubation, the culture was boiled, homogenized and centrifugated to obtain a supernatant liquid. The thus obtained supernatant liquid was subjected to the determination of cyclic AMP by the method of Gilman. The results are shown in FIG. 10. A function of the present substance of raising the level of cyclic AMP in the tumour cells of sarcoma 180 was recognized. The participation of the present substance in the metabolism of PGs is presumed also from this fact.

EXAMPLE 7

The influence of the present substance on the $PGI_2$-productivity of 3T3 fibroblasts:

The influence of the present substance on the $PGI_2$-productivity of the 3T3 fibroblasts of a mouse was examined. As the control, a culture was used in which arachidonic acid, the precursor of PGs, is added to a cultured medium of mouse-3T3 fibroblasts, and the mixture was incubated for 5 min at 37° C. to produce $PGI_2$.

On the other hand, 30 mmol of each of the present substances (Specimens Nos. 1, 3, 4 and 7 to 11) was added to 4 ml of a cultured medium of 3T3 cells, and the mixture was incubated for 2 min. at 37° C. After adding arachidonic acid to the incubated culture, it was again incubated as in the control to produce $PGI_2$. The just mentioned culture was named as the treated group.

After obtaining the respective supernatant liquids of the cultures, the control and the treated group, their productivities of $PGI_2$ were compared while using the suppressing action on the aggregation of the platelets induced by the addition of 2.43 mmol of arachidonic acid, as an indicator.

Figure 11:
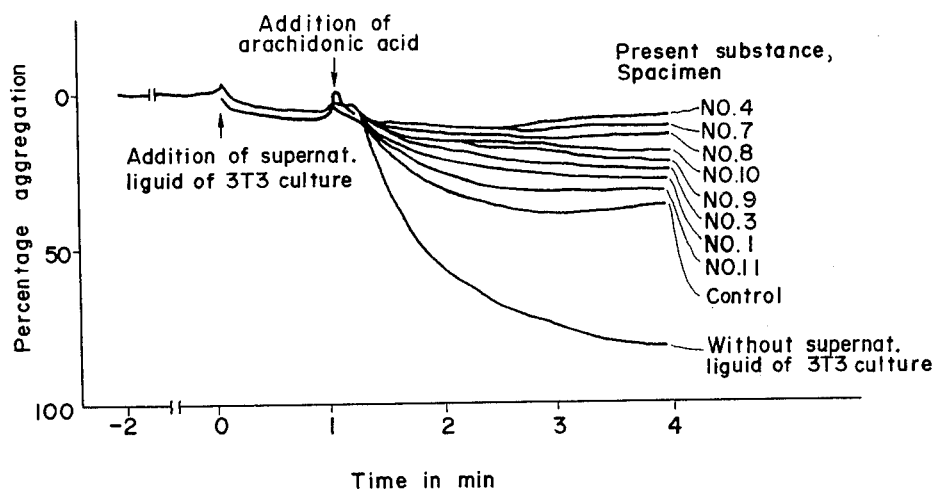
FIG. 11 shows the effect of the present substance on the production of prostaglandin $I_2$ ($PGI_2$) in 3T3-fibroblasts.

The results are shown in FIG. 11, and as is seen in FIG. 11, although the suppression of platelet-aggregation was recognized to an extent in the control after 5 min of the addition of arachidonic acid as a precursor of PGs, a remarkable suppression was recognized in the treated group to indicate the raised productivity of PGI$_2$ by the addition of the present substance.

EXAMPLE 8

The effect of the present substance on the metabolism of cyclic AMP and cyclic guanosine monophosphate in cancer-bearing mouse:

Ehrlich cancer cells were transplanted into the abdominal cavity of female ICR/JCL mice after 5 weeks of birth at a rate of $1 \times 10^6$, cells/animal, and while feeding the mice, the present substance, Specimen No. 7, was intraperitoneally administered to the mice every day from the next day of transplantation for 5 days at a rate of 200 mg/kg/day. On the 6th day, the mice were sacrificed with ether to collect each 5 ml of ascites. After adding tetrasodium ethylenediaminetetraacetate into the thus collected ascites, the mixture was centrifugated for 10 min at a temperature of 4° C. and 1,500 rpm to separate the supernatant liquid and the cancer cells. The supernatant liquid was again centrifugated at 4° C. and 3,000 rpm for 15 min. The separated cancer cells were washed with Hank's solution and then subjected to repeated centrifugation for 5 times at 800 rpm for each 5 min to remove impurities such as erythrocytes, etc. After homogenizing $1 \times 10^8$ cells of the cancer in 3 ml of an aqueous 6% solution of trichloroacetic acid at a temperature of 0° C., the homogenate was centrifugated for 20 min at 3000XG to obtain a liquid extract. After adding 10% by weight of an aqueous 1 N solution of hydrochloric acid to the liquid extract, it was extracted 5 times with each two times by volume of ether to remove trichloroacetic acid. After completely removing ether by warming the residual liquid on a water bath of 80° C., the residue was freeze-dried.

To the supernatant of ascites, an equal amount of an aqueous 10% solution of trichloroacetic acid was added, and after leaving for 15 min at a temperature of 0° C., it was centrifugated for 20 min at 3000XG to obtain a supernatant liquid. To the thus obtained supernatant liquid, 0.1 ml of an aqueous 1 N solution of hydrochloric acid was added, and after removing trichloroacetic acid with 2 times by volume of ether, ether was completely removed on a water bath of 80° C., and the residue was freeze-dried.

Both the freeze-dried specimens derived respectively from the cancer cells and the supernatant of ascites were respectively dissolved into 1 ml of an aqueous buffer solution of pH of 4.0 containing 50 mmol of acetic acid and subjected to the radio-immuno assay using anti-cyclic AMP anti-body and anticyclic guanosine monophosphate (GMP) anti-body for determining cyclic AMP and cyclic GMP respectively in the cancer cells and in the supernatant liquid of ascites. The results are shown in Table 5A. The raise of the contents of cyclic AMP and cyclic GMP in the cancer cells was recognized, the cancer cells being derived from the rat to which the present substance has been administered. From this fact, the influence of the present substance on the metabolism in vivo of cyclic AMP and cyclic GMP of the cancer cells derived from the transplanted cancer cells in the mouse's body was recognized.

TABLE 5A

| | Level of cyclic AMP and cyclic GMP | |
| --- | --- | --- |
| Group | Cyclic AMP per $10^8$ cancer cells | unit: pM GMP per $10^8$ cancer cells |
| Control | 19.5 | 0.59 |
| Present substance | 21.2 | 0.72 |

EXAMPLE 9

Effect of the present substance on the amount of PGs in a culture medium wherein human leukemia cells are cultured:

To each 10 ml of a culture medium prepared by adding 10% of bovine foetal serum and one of the present substance, Specimen No. 7, at a concentration of 50, 500 or 5,000 μg/ml to Eagle's culture medium and placed in a polystyrene flask of 75 cm$^2$ in bottom surface, $5 \times 10^5$ cultured cells of human dinuclear leukemia J-111 strain were inoculated and cultured at 37° C. under a mixed atmosphere of 5% by volume of gaseous carbon monoxide and 95% by volume of air for 7 days. During the cultivation, the culture medium was replaced on the second day and the fourth day with respective fresh ones, and each spent medium was subjected to centrifugation as soon as possible at a temperature of 4° C. at 1,500 rpm to obtain each supernatant liquid of cultured medium. The content of PGE and PGF$_{2-\alpha}$ in each supernatant liquid was determined by $^3$H-Prostaglandin E Radioimmunoassay Kit and $^3$H-Prostaglandin F Radioimmunoassay Kit (manufactured by Clinical assay Co. U.S.A.).

Figure 12:
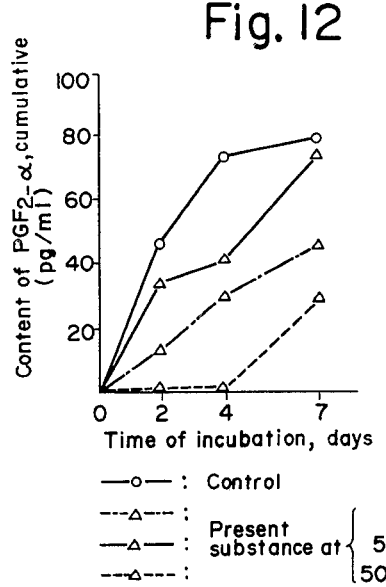
FIG. 12 shows the effect of the present substance on the level of prostaglandin $F_{2-\alpha}$ ($PGF_{2-\alpha}$)
Figure 13:
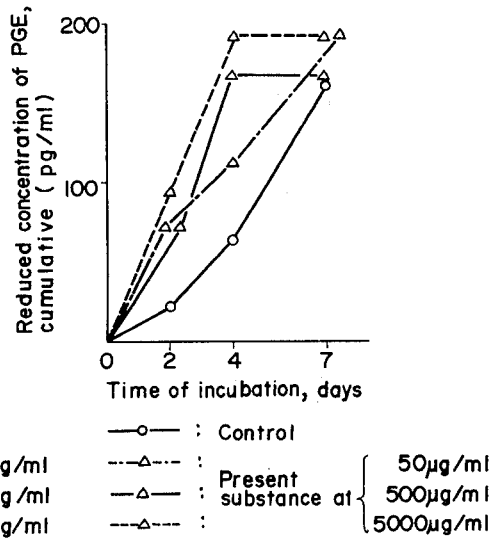
FIG. 13 shows the effect of the present substance on the level of prostaglandin E (PGE)

The results are shown in FIGS. 12 and 13. As is seen in FIG. 12, the cumulated amount of PGF$_{2-\alpha}$ increased as the time passed, and as is seen in FIG. 13, the cumulated amount of PGE decreased as the time passed, in general. However, the rate of increase of PGF$_{2-\alpha}$ was reduced as the concentration of the present substance was increased, and the rate of decrease of PGE was raised as the concentration of the present substance was increased. At any rate, the participation of the present substance in the metabolism of PGs is observed from FIGS. 12 and 13.

EXAMPLE 10

Effect of the present substance on the amount of PGs in a culture medium wherein human uterine cancer cells are cultured:

To each 10 ml of a culture medium prepared by adding 10% bovine foetal serum and one of the present substance, Specimen No. 7, at a concentration of 0 (control), 10, 100, 500, 1,000 or 5,000 μg/ml to Eagle's culture medium and placed in a polystyrene flask of 75 cm$^2$ in bottom surface, HeLa S3 cultured cells of human uterine cancer were inoculated at a rate of $5 \times 10^5$ cells/flask and cultured at 37° C. for 2 days under a mixed atmosphere of 5% by volume of gaseous carbon dioxide and 95% by volume of air. After the incubation was over, the whole cultured medium was centrifugated at a temperature of 4° C. at 1,500 rpm to obtain a supernatant liquid of the cultured medium. The content of PGE in the supernatant liquid was determined by $^3$H-Prostaglandin E Radioimmunoassay Kit. The results are shown in Table 6.

As is seen in Table 6, the amount of PGE in the culture medium (without cancer cells) was reduced by the addition of the present substance. This fact shows the effect of the present substance on the metabolism of PGs.

TABLE 6

Content of PGE in the culture medium (without cells)

| Concentration of the present substance (μg/ml) | Concentration of PGE after culture (pg/ml) | Change of Concentration of PGE during culture (pg/ml) |
|---|---|---|
| 0 (control) | 312 | +120 |
| 10 | 40 | −152 |
| 100 | 80 | −112 |
| 500 | 48 | −144 |
| 1000 | 25 | −167 |
| 5000 | 25 | −167 |

EXAMPLE 11

Effect of the present substance on PGE in cancer cells and in ascites of mouse transplanted with Ehrlich cancer cells:

To groups of female ICR-JCL mouse after 5 weeks of her birth, Ehrlich cancer cells were intraperitoneally transplanted at a rate of $1 \times 10^6$ cells/animal and one of the present substances, Specimen No. 7 was administered intraperitoneally to the mice every day from the next day of transplantation for 5 days at a rate of 200 mg/kg/day. The mice were sacrificed with ether on the 6th day of transplantation, and the ascites were collected. After adding tetrasodium ethylenediamminetetraacetate with 1% by weight of aspirin into the ascites, it was centrifuged for 10 min at 1500 rpm and a temperature of 4° C. to separate the cancer cells and the supernatant liquid. The supernatant liquid was further centrifugated at 4° C. and 3000 rpm for 15 min. The separated cancer cells was washed with Hank's solution, and was subjected to centrifugation 5 times at 800 rpm for each 5 min to remove impurities such as erythrocytes, etc. The thus purified cancer cells of $1 \times 10^8$ in number were homogenized at 0° C. after addition of 7 ml of methanol, and the homogenate was filtered with filter paper. After adding 14 ml of chloroform to the filtrate and mixing, the mixture was left for 30 min at a temperature of 4° C. Then, the precipitated protein was removed by suction-filtration, and the thus obtained filtrate was dried to solid in a rotary evaporator. The dried solid material was put into a separating funnel together with chloroform, methanol and an aqueous dilute solution of hydrochloric acid of pH of 2, and after well mixing it was dissolved into the lower aqueous layer of a solution of 2 ml. The content of PGE in the solution and in the supernatant liquid of the ascites was determined by $^3$H-Prostaglandin E Radioimmunoassay Kit. The results are shown in Table 7. In the animal transplanted with cancer cell and administered with the present substance, PGE is contained in larger amount in the cancer cells and is contained in smaller amount in the supernatant liquid of the ascites as compared to those in animal transplanted with the same cancer cells but not administered with the present substance. This fact suggests strongly the relationship between the administration of the present substance and the metabolism of PGs.

TABLE 7

Content of PGE in cancer cells and ascites (supernatant)

| Group | Content of PGE in $10^8$ cells (ng) | Content of PGE in supernatant liquid of ascites (ng) |
|---|---|---|
| Control | 2.36 | 0.26 |
| Present substance | 3.06 | 0.12 |

EXAMPLE 12

Effect of the present substance on the amount of PGE in Ehrlich cancer cells and against the tumor proliferation:

Ehrlich cancer cells were transplanted subcutaneously to groups of female C57BL/6 mouse after 9 weeks of birth at a rate of $1 \times 10^6$ and while feeding the mice, the present substance, Specimen No. 7, was intraperitoneally administered to the mice every other day from the next day of the transplantation at a rate of 100 mg/kg. On 14th day of the transplantation, the mice were sacrificed with ether to extirpate the tumor tissue. After homogenizing the tumour tissue finely cut by scissors with the addition of 7 ml of methanol per gram of the tumour tissue at a temperature of 0° C., the homogenate was filtered with filter paper to obtain a filtrate. After adding 2 times by volume of chloroform to the filtrate, the mixture was well mixed and left for 30 min at 4° C. Then, the cooled mixture was subjected to the same procedures as in Example 11 to determine the content of PGE in the tumour tissue. The results are shown in Table 8. The content of PGE in the tumour tissue was larger in the animal transplanted with the cancer cells and administered with the present substance than in the control transplanted with the same cancer cells but not administered with the present substance. This face gives an information concerning the participation of the present substance in the metabolism of PGs.

TABLE 8

Content of PGE in tumour tissue

| Group | Weight of tumour tissue (g) | Content of PGE in the tumour tissue (ng/g) |
|---|---|---|
| Control | 1.30 | 1.77 |
| Given the present compound | 0.75 | 3.98 |

EXAMPLE 13

Repetition of the experiment in Example 12 with a slight different conditions:

Ehrlich's cancer cell were transplanted subcutaneously to groups of female C57BL/6 mouse after 8 weeks of her birth and while feeding the mice, the present substance, Specimen No. 7, was orally administered to each mouse every day at a rate of 1 g/kg/day. On 7th or 14th day of the transplantation, the mice were sacrificed with ether to extirpated the tumour. The tumour was treated by the same procedures as in Example 11 to determine the content of PGE therein. The results are shown in Table 9. The concentration of PGE in the tumour was larger in the animal transplanted with the cells and administered with the present substance than in the control to which the same cells were transplanted but the present substance was not administered. Further it is observed that the content of PGE decreased in both groups as the time passed, and the rate of decrease was smaller in the group transplanted and administered than in the control group transplanted but not administered. These facts give the information that the present substance participates to the metabolism of PGE.

TABLE 9

| Group | Date of extirpation after transplantation | Weight of tumour (g) | Content of PGE in the tumour (ng/g) |
|---|---|---|---|
| Control | 7th day | 0.09 | 2.59 |
|  | 14th day | 0.84 | 1.16 |
| Given the present substance | 7th day | 0.08 | 2.80 |
|  | 14th day | 0.67 | 1.65 |

EXAMPLE 14

Effect of the present substance on the content of PGE in the tumour of adenocarcinoma 755 and against its proliferation:

Tumour cells of Adenocarcinoma 755 were transplanted subcutaneously to groups of female C57BL/6 mouse of after 8 weeks of birth and while feeding the mice, the present substance, Specimen No. 7, was orally administered every day from the next day of transplantation at a rate of 1 g/kg/day. The mice were sacrificed with ether on 7th or 14th day of transplantation to extirpate the tumour. The thus extirpated tumour was treated by the same procedures as in Example 11 to determine the content of PGE in the tumour. The results are shown in Table 10. As is seen in Table 10, the content of PGE in the tumour showed a decrease as the time passed in both groups of which one had transplantation and administration and the other had transplantation but no administration, and the level of the content of PGE was consistently higher in the group administered with the present compound than in the control. These facts shows the participation of the present compound in the metabolism of prostaglandins.

TABLE 10

| Group | Date of extirpation after transplantation | Weight of tumour (g) | Content of PGE in tumour (ng/g) |
|---|---|---|---|
| Control | 7th day | 1.34 | 0.67 |
|  | 14th day | 4.01 | 0.34 |
| Given the present substance | 7th day | 1.04 | 2.83 |
|  | 14th day | 3.10 | 1.15 |

EXAMPLE 15

Effect of the present substance on the translocation of a dye-staff from the injected region to the transplanted tumour:

On the back of a donryu rat, a lump of Sato's lung cancer of 5 mm in size was subcutaneously transplanted.

On the axillary part of an ICR mouse, $10^6$ cells of sarcoma 180 were subcutaneously transplanted. While feeding the both animals, the present substance, Specimen No. 7, was forcibly administered orally once at a rate of 1000 mg/kg on 16th day of the transplantation and an aqueous 2% solution of Lissamine Green (a dye-staff manufactured by Imperial Chem. Ind. Co.) was injected into the caudal vein of the animal at a rate of 1 ml for a rat and 0.5 ml for a mouse.

After one hour of the injection, the animal was sacrificed to extirpate the proliferated tumour. The tumour of the rat was finely cut and homogenized with an aqueous 50% solution of ethanol. After diluting the homogenate with an addition of the solution to a total volume of 50 ml, the liquid was centrifugated for 15 min at 1000 rpm to separate the supernatant liquid. The content of the dye-staff was determined on the supernatant liquid itself or after dilution by spectrophotometry using its absorption maximum of 630 nm. Concerning the tumour of the mouse, the tumour was cut and the presence of the dye-staff was observed with naked eyes on the cross section of the tumour.

The amount of the dye-staff sedimented in Sato's lung cancer per g of the cancer is shown in Table 11.

TABLE 11

| Group | Amount of dye-staff (μg/g tumour) |
|---|---|
| Control | 30.0 |
| Given the present substance | 51.0 |

By visual observation, the remarkable sedimentation of the dye-staff in the central part of the tumour was recognized in the case of sarcoma 180 in the mouse administered with the present substance. The results show that the present substance will promote the attainability of the anti-cancer drug to a tumour and suggest the participation of the present substance in the metabolism of PGE.

EXAMPLE 16

Effect of the present substance in preventing the metastasis of a transplanted tumour:

Cells of MH-134 tumor were transplanted to a C$_3$H/He mouse from its caudal vein at a rate of $2 \times 10^6$ cells/animal. The present substance, Specimen No. 7, was administered to the mouse respectively, 6, 3 and one hours before, and 1, 3 and 6 hours after the transplantation once at a rate of 1000 mg/kg forcibly p.o.

The mouse was sacrificed on 14th day of the transplantation to extirpate the lungs to examine the number of the metastatic lesion. The rate of positive metastasis and the number of metatic lesion are shown in Table 12.

TABLE 12

| Group | Rate of positive metastasis (%) | Number of metastatic lesion |
|---|---|---|
| Administered |  |  |
| 6 hours before | 10/10 (100%) | 2.3 |
| 3 hours before | 8/9 (88.9%) | 1.9 |
| 1 hour before | 7/9 (77.8%) | 2.2 |
| 1 hour after | 7/10 (70%) | 2.6 |
| 3 hours after | 9/10 (90%) | 3.0 |
| 6 hours after | 10/10 (100%) | 3.5 |
| Not administered | 6/6 (100%) | 4.5 |

Since there are several informations concerning the participation of PGs, particularly of PGD$_2$ on the metastasis of a transplanted tumour, the above-mentioned data are considered to suggest the inhibiting effect of the present substance against the metastasis of an inplanted tumour via PGs.

EXAMPLE 17

Variation of the level of PGs in the blood of the animal administered with the present substance:

Cells of sarcoma induced by methylcholanthrene were transplanted on the back of a group of spontaneous hypertensive rats (SHR) subcutaneously at a rate of $1 \times 10^6$ cells/animal, and while feeding the rats, the present substance, Specimen No. 7, was daily administered intraperitoneally for consecutive 6 days from after 24 hours of the transplantation at a rate of 500 mg/kg/day. After 2 weeks of the ending of administration, whole blood was collected to obtain a fraction of plasma. The ether-extract of the plasma was separated by thin layer chromatography and after converting the extract into a methyloximesilyl derivative, the variation of the level 6-keto $PGF_{1\alpha}$ in the extract was examined by gas-chromatography and masspectroscopy. The results are shown in FIG. 14.

Figure 14:
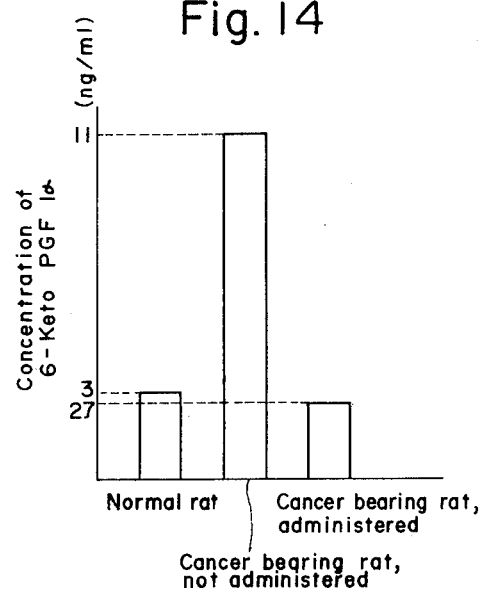
FIG. 14 shows the effect of the present substance on the level of PGs in the plasma of rat administered with the present substance.

It is seen in FIG. 14 that although, in general, the level of 6-keto $PGF_1$ in the blood of rat under a cancer-bearing burden is higher than that of rat in normal state in the blood, the level in cancer-bearing rat administered with the present substance was almost same as in normal rat. It is presumed that the present substance has reduced the raised level to the normal one.

EXAMPLE 18

Effect of the present substance on cancer proliferation and the amount of PGE in the cancer cells:

Following the same method as in Example 12, the anti-cancer action against transplanted Ehrlich cancer in C57BL/6 mouse, and the amount of PGE in the cancer cells in proliferation in the living body of the mouse were examined in the cases where each one compound of the present invention, Specimens Nos. 1, 2, 3, 4, 5, 6, 8, 9, 10 and 11 was intraperitoneally administered every other day from the next day of the transplantation in total 6 times at a dosage of 100 mg/kg.

The results of determination of the weight of cancer extirpated from the sacrificed mouse on 14th day of the transplantation of the cancer cells, $1 \times 10^6$ in number per animal, and content of PGE of the extirpated cancer are shown in the following Table 13:

TABLE 13

| | Weight of cancer (g) and content of PGE in cancer (ng/g) | |
|---|---|---|
| Compound | Weight of cancer (g) | Content of PGE in the cancer (ng/g) |
| Control[1] Specimen | 1.30 | 1.77 |
| No. 1 | 0.63 | 4.10 |
| No. 2 | 0.81 | 3.88 |
| No. 3 | 0.74 | 4.23 |
| No. 4 | 0.56 | 4.19 |
| No. 5 | 0.70 | 3.20 |
| No. 6 | 0.65 | 3.66 |
| No. 7[2] | 0.75 | 3.98 |
| No. 8 | 0.72 | 4.03 |
| No. 9 | 0.80 | 4.32 |
| No. 10 | 0.70 | 4.14 |
| No. 11 | 0.69 | 4.20 |

Notes:
[1]animals transplanted, but not administered.
[2]results of Example 12

As is seen in the table, although there are some differences between the compounds, they are all effective in inhibiting the growth of the cancer and in raising the level of the content of PGE in the cancer cells.

EXAMPLE 19

Effect of aspirin on the hypotensive action of the present substance:

It is known that PGs are produced from arachidonic acid and the conversion of arachidonic acid into $PGG_2$ is mediated by cyclooxygenase. Also it is known that aspirin inactivates cyclooxygenase, and that the metabolism of PGs is completely stopped by the administration of aspirin to a mammal.

Accordingly, the following experiment was carried out: To groups of male SHR rats of 30 to 40 weeks after birth, (a) one of the present substance was forcibly administered orally at 100 mg/kg as a solution in distilled water or an aqueous suspension in 2% solution of carboxymethylcellulose or (b) aspirin was forcibly administered orally, before and after one hour of the administration of the present substance, at 200 mg/kg. The blood pressure of the thus treated rats was measured with the time passage.

The results are shown in Table 14. As is seen in Table 14, by the administration of inhibitor of the metabolism of PGs, aspirin, the hypotensive effect of the present substance (Specimens Nos. 4, 7 and 8), which appeared in the group (a), did not appear in the group (b). The results show that the hypotensive effect of the present substance is due to PGs.

TABLE 14

| | Hypotensive effect inhibited by aspirin | |
|---|---|---|
| | Alteration of blood pressure (mmHg)[1] | |
| Compound | Case (a) | Case (b) |
| Control[2] Specimen | 0 | 0 |
| No. 4 | −20 | −5 |
| No. 7 | −20 | 0 |
| No. 8 | −15 | 0 |

Notes:
[1]after 6 hours of the administration of the present substance.
[2]only given distilled water at the same time of the administration of aspirin and the present substance.

EXAMPLE 20

Effect of the present substance on the level of PGs in the blood of spontaneously hypertensive rat (SHR):

After forcibly administering the present substance (Specimens Nos. 4, 7 and 8) every day for successive 14 days at a rate of 100 mg/kg/day by oral route to groups of male SHR rats, their whole blood was collected on 15th day to obtain the plasma fraction. The ether-extract of the plasma fraction was separated and isolated by thin-layer chromatography and after converting the isolated fraction into methyloximesilyl derivatives, the alteration of 6-keto $PGF_{1-\alpha}$ was examined by gas-chromatography and mass-spectroscopy. The results are shown in Table 15. In the group to which the present substance was administered, the content of 6-keto $PGF_{1-\alpha}$ was larger together with the reduced blood pressure than in control. This parallelism of the effects leads to the presumption that the effect of the present invention is mediated by prostaglandin.

TABLE 15

| Blood pressure and content of PGs in the blood collected after 14 days of administration of the present substance (Specimens Nos. 4, 7 and 8) | | | | |
|---|---|---|---|---|
| | Control | Specimen No. 4 | No. 7 | No. 8 |
| Blood pressure (mmHg) | 195 | 155 | 160 | 150 |
| Content of 6-keto-$PGF_{1-\alpha}$ in blood | 3 | 7 | 6.5 | 7 |

TABLE 15-continued

Blood pressure and content of PGs in
the blood collected after 14 days of
administration of the present substance
(Specimens Nos. 4, 7 and 8)

| | Control | Specimen No. 4 | No. 7 | No. 8 |
|---|---|---|---|---|
| (ng/ml) | | | | |

EXAMPLE 21

Effect of the present substance on the production of $PGI_2$ in rat suffuring from diabetes mellitus:

Groups of male Sprague-Dowley rats of body weight of about 200 g are used for the present experiments. Some groups of the rats were intravenously administered with streptozotocin at 80 mg/kg one to three months in advance of the beginning of the present experiment to be in a state of diabetes mellitus. Those rats of the same strain, the same sex and the same age without being administered with streptozotocin were used as control.

The present substances (Specimens Nos. 4, 7 and 8) were respectively administered to the groups of rats suffering from the artificial diabetes mellitus forcibly by oral route at a rate of 100 mg/kg as an aqueous solution in distilled water.

After 6 hours of the administration of the present substance, blood specimen was collected from the rat under anesthesia by ether in an amount of 0.5 ml/animal, and the content of blood sugar was measured by the enzymatic method.

In the next place, the amount of prostaglandin $I_2$ produced in the arterial tissue was measured as follows:

Thoracic aorta of the rat was rapidly extirpated, washed with Krebs' buffer solution at a temperature of 4° C. and cut into thin rings of 1 to 2 mg in weight. Then, into 200 microliters of Krebs' buffer solution, 60 mg of the thus cut aorta were added and the mixture was incubated for 3 min at 22° C.

The amount of prostaglandin $I_2(PGI_2)$ produced by the cut aorta was determined on the supernatant liquid (1 to 10 microliters) of the above-mentioned incubated culture in the same manner as in Example 2 using the suppressing action of platelet aggregation as an index, however, using adenosine diphosphate as the agglutinating agent. After preparing a standard calibration curve using an authentic specimen of $PGI_2$, the content of $PGI_2$ of the above-mentioned supernatant liquid was obtained from the standard curve in ng/mg of wet weight of the arterial tissue. The results are shown in Table 16.

TABLE 16

Amounts of $PGI_2$ and blood sugar:

| Group of rats | $PGI_2$ (ng/mg wet tissue) | Blood sugar (mg/100 ml) |
|---|---|---|
| Normal rat | 0.26 ± 0.06 | 76.7 ± 5.0 |
| Rat in artificial diabetes mellitus | | |
| Not administered with the present substance | 0.07 ± 0.01 | 412.1 ± 15.1 |
| Administered with Specimen No. 4 | 0.19 ± 0.04 | 133.6 ± 8.3 |
| Administered with Specimen No. 7 | 0.22 ± 0.02 | 165.0 ± 11.0 |
| Administered with Specimen No. 8 | 0.18 ± 0.04 | 110.1 ± 5.5 |

Although the production of $PGI_2$ in the aortic tissue of the rat artificially brough into the state of diabetes mellitus was lower than that of the normal rat, administration of the present substance into the rat artificially brough into the state of diabetes mellitus raised the capability of the tissue in producing $PGI_2$ together with the reduction of the level of blood sugar.

EXAMPLE 22

Another example showing the effect of the present substance on the production of $PGI_2$:

After extirpating the cervical aorta of an SD rat under anesthsia, it was washed with Krebs-Linger bicarbonate buffer solution and cut into thin rings, and the cutings were kept in the above-mentioned buffer solution at a rate of 1 mg of wet cuttings per 0.5 ml to produce $PGI_2$.

Figure 15:
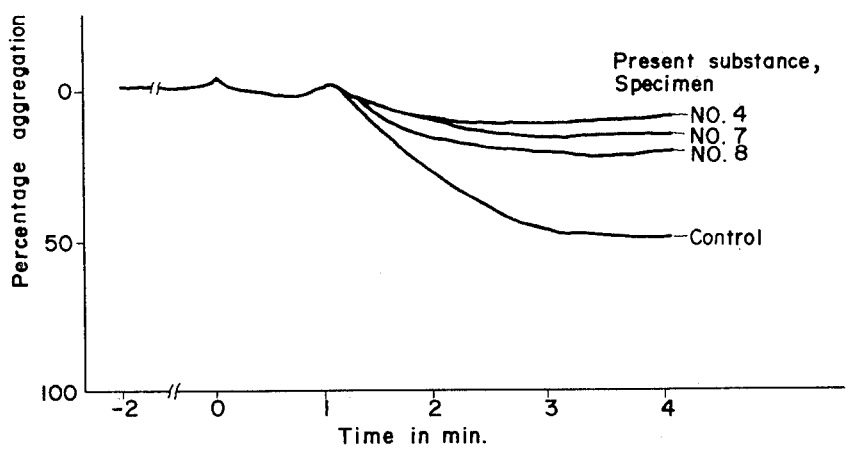
FIG. 15 shows the effect of the present substance in prevention of the aggregation of the platelets induced by ADP.

Into 500 microliters of the thus prepared mixture, 50 micro-liters of an aqueous physiological saline solution containing 2% by weight of the present substance (each of Specimens Nos. 4, 7 and 8) dissolved therein were added and, since the production of $PGI_2$ generally attains to its maximum after 10 min of keeping, a supernatant liquid (2.5 $\mu$l) of the mixture was prepared after 10 min of the addition, and then the amount of $PGI_2$ in the supernatant liquid was determined by using the action of suppression of aggregation of the platelets as an index and using ADP as the agglutinating agent, only an aqueous physiological solution being used as control. The results are shown in FIG. 15. The addition of the present substance raised the production of $PGI_2$ by the cuttings of cervical aorta.

In addition, although various examinations have been carried out on the cause of arteriosclerosis, the agglutination of the aggregated clumps to the wall of vessels is mentioned as a cause of special importance. In other words, the prevention of the agglutination of the platelets onto the wall of vessels is the first treatment. It has been known that $PGI_2$ has a strong inhibitory function against the agglutination of the platelets, and from the information, it is clearly understood that the present substance which raises the producibility of $PGI_2$ on the aortal wall has an effect of treatment and an effect of preventing of arteriosclerosis.

EXAMPLE 23

Effect of the present substance in raising the level of $PGE_1$ in the living body of mammals:

(1) In the case of artificially caused foot-oedema

The three groups of male Sprague-Dowley rats of total six groups, the respective present substances, Specimens Nos. 4, 7 and 8 were administered forcibly by oral route at a rate of 1000 mg/kg, the other three groups of the same kind of rats being administered nothing at this time.

After 60 min of the administration, 0.1 ml of an aqueous solution of carrageenin (1 mg) and $PGE_1$ (0.1 $\mu$g) was injected onto the hind paw of the four groups of the rats including the three groups administered with the present substance. To one group of remaining two groups not administered with the present substance, 0.1 ml of an aqueous solution containing only carrageenin at 1% was injected, and to the other one group not administered with the present substance, an aqueous solution containing only $PGE_1$ was injected.

The volume of the thus swollen foot of the groups of the thus treated rats was measured by the water-displacement method, and the results are shown in Table 17 by the increment of the volume of foot as compared to the volume of foot before the treatment as percentage.

(2) In the case of stimulating the skin:

To the three groups of male Sprague-Dowley rats of the total six groups, the respective present substances (Specimens Nos. 4, 7 and 8) were forcibly administered by oral route at the rate of 1000 mg/kg, the other three groups being administered nothing at this time. After 60 min of the administration, a mixture of $PGE_1$ ($2.5 \times 10^{-11}$ mol/animal) and histamine ($2 \times 10^{-8}$ mol/animal) was intracutaneously injected under light etheranesthesia into the shaved skin of an abdominal part of four groups of the rats including three groups administered with the present substance. To the one group of the two groups remaining intact, only histamine was injected at a rate of $2 \times 10^{-8}$ mol/animal, and to the other group, only $PGE_1$ at a rate of $2.5 \times 10^{-11}$ mol/animal was injected.

Immediately after the above-mentioned injection, Evans blue as an aqueous solution in aqueous physiological saline solution was injected into a lateral tail vein of all the experimental rats in an amount of 2 ml/kg, corresponding to 25 mg of Evans blue/kg. All the animals were sacrificed after 30 min of the injection of the dye-staff, and the extent of the dye leakage was examined spectrophotometrically according to the method of Harada et al. using the absorbance at 620 nm as the index.

The results are shown in Table 18.

TABLE 17

Effect of the present substance on swelling induced by carrageenin

| Groups of rats treated by | Percentage increment of volume of foot after 60 min of administration of carrageenin |
|---|---|
| Carrageenin | 37.0 |
| $PGE_1$ | 9.3 |
| Carrageenin + PGE | 66.2 |
| Specimen No. 4 + Carrageenin + $PGE_1$ | 32.5 |
| Specimen No. 7 + Carrageenin + $PGE_1$ | 28.2 |
| Specimen No. 8 + Carrageenin + $PGE_1$ | 29.7 |

TABLE 18

Effect of the present substance on leakage of dye-staff

| Group of rats treated by | Absorbance at 620 nm |
|---|---|
| Histamine | 0.192 |
| $PGE_1$ | 0.066 |
| Histamine + $PGE_1$ | 0.259 |
| Specimen No. 4 + histamine + $PGE_1$ | 0.155 |
| Specimen No. 7 + histamine + $PGE_1$ | 0.152 |
| Specimen No. 8 + histamine + $PGE_1$ | 0.162 |

The results shown in Table 17 indicate that the inflammation caused by carrageenin and potentiated by $PGE_1$ was inhibited by the action of the present substance.

The results shown in Table 18 indicate that the dye-leakage due to histamine and potentiated by $PGE_1$ was inhibited.

EXAMPLE 24

Diuretic effect of the present substance in connection to the level of 6-keto $PGF_{1\alpha}$ in blood of rats.

Groups of female spontaneously hypertensive rats (SHR) kept in fasting for 12 hours and abstained from water for 2 hours were treated by forced oral administration of the present substance (each of Specimens Nos. 4, 7 and 8) at respective rates of 1 and 5 g/kg dissolved in 8 ml (per 200 g b.w.) of an aqueous physiological saline solution, control group being administered only with the aqueous physiological saline solution in an amount of 8 ml/200 g b.w.

The amount of excreted urine of the rats was measured every hour from one hour after the administration for 6 times, and the percentages of the volume of urine to the volume of the aqueous physiological saline solution containing the present substance formerly administered (8 ml per 200 g b.w.) are shown in Table 19.

In the next place, after 6 hours of the administration, all animals were sacrificed to collect the whole blood for obtaining its plasma fraction. The ether-extract of the plasma fraction was separated by thin-layer chromatography and after converting the thus separated substances into methyloximesilyl derivatives, the variation of 6 keto $PGF_{1\alpha}$ was examined by gas-chromatography-mass-spectrography. The results are shown also in Table 19.

As is seen in Table 19, the amount of urine, after converting to the standard value of recovery, was larger in the rats administered with the present substance than in control, and a dosage-effect relationship is seen in the amount of urine among the rats administered with the present substance. In other words a diuretic effect is recognized in the present substance.

In addition, the level of 6-keto $PGF_{1\alpha}$ in the blood of the rats administered with the present substance is a little larger than that of control although the difference is very small. Although it is natural that the raise of 6-keto $PGF_{1\alpha}$ which is the metabolite of $PGI_2$ means the raise of the level of $PGI_2$, since the diuretic function is recognized as one of the physiological functions of $PGI_2$, it is presumable that the present substance exhibits its diuretic effect by regulating $PGI_2$.

TABLE 19

Amount of urine and level of 6-keto $PGF_{1\alpha}$ in blood.

| Groups | Volume of urine[1] (%) at hours of | | | | | | Level of 6-keto $PGF_{1\alpha}$ in blood (ng/ml) |
|---|---|---|---|---|---|---|---|
| | 1 | 2 | 3 | 4 | 5 | 6 | |
| Control | 2 | 9 | 22 | 26 | 28 | 30 | 3.0 |
| Present substance | | | | | | | |
| Specimen No. 4 | | | | | | | |
| 5 g/kg | 7 | 40 | 50 | 52 | 78 | 91 | 3.5 |
| 1 g/kg | 6 | 40 | 46 | 50 | 60 | 63 | 3.3 |
| Specimen No. 7 | | | | | | | |
| 5 g/kg | 5 | 50 | 66 | 80 | 92 | 100 | 3.9 |
| 1 g/kg | 4 | 38 | 45 | 48 | 63 | 72 | 3.5 |
| Specimen No. 8 | | | | | | | |
| 5 g/kg | 5 | 43 | 60 | 70 | 77 | 93 | 3.7 |
| 1 g/kg | 5 | 39 | 47 | 50 | 65 | 68 | 3.2 |

Note:
[1] The percentage of the volume of accumulated urine at the time of determination to the volume of administered aqueous physiological saline solution containing the present substance.

EXAMPLE 25

Effects of the present substance on the pain threshold of pain caused by repeated injection of $PGE_2$:

Group of male Wistar rats of body weight of 230 to 250 g were injected daily for 2 weeks onto their both paws with 2 μg of $PGE_2$ dissolved in 0.1 ml of an aqueous sterilized 0.9% solution of sodium chloride. On the 16th day, the present substance (each of Specimens Nos.

4, 7 and 8) was forcibly administered orally at the rate of 1000 mg/kg.

"Pain threshold" was measured one hour after the administration of the present substance. The word "pain threshold" means the minimum pressure applied on the paw of the rat causing distress of the rat. The results are shown in FIG. 16.

Figure 16:
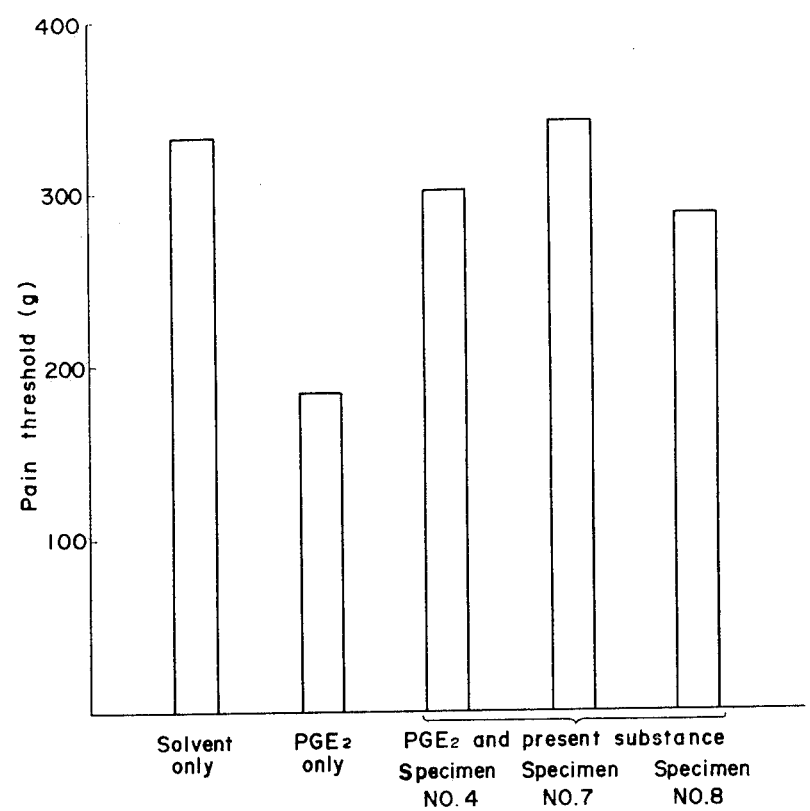
FIG. 16 shows the effect of the present invention in reducing the level of PGE in cerebrospinal fluid once raised by a pyrogenic microbes.

As is seen in FIG. 16, the reduction of "pain threshold" caused by the injection of PGE$_2$ was restored almost to zero by the administration of the present substance. In other words, an analgetic effect of the present substance was found.

EXAMPLE 26

Effect of the present substance in preventing the occurrence of stress ulcer of the stomach of rats:

Three groups of male Donryu rats of body weight of 220 to 250 g after 23.5 hours of fasting were administered orally with the present substance (each of Specimen Nos. 4, 7 and 8) at a rate of one gram/kg dissolved in 8 ml (per 200 g body weight) of an aqueous physiological saline solution.

These three groups of rats and another group of rats equally fasted for 23.5 hours and then administered with only the aqueous physiological saline solution were put into the stresscage, and soaked in water at a temperature of 23° C. to the depth of their breast to load the stress on the rats.

After 7 hours of soaking, the rats were pulled out from water and were immediately sacrificed to collect the whole blood, and their stomachs were extirpated. The plasma fraction prepared from the blood was extracted with ether and the etherextract was separated by thin layer chromatography. The separated extract, after converted to the respective methyloximesilyl derivatives, was subjected to gaschromatography-mass spectorography to determine the content of 6-keto PGF$_{1\alpha}$.

An aqueous 1% solution of formaldehyde was injected into the extirpated stomach and after 10 min of injection, the stomach was cut to be opened at the greater curvature side to examine the mucous membrane of the gastric body. The longer span of each erosion in the mucous membrane of a rat, if any, was measured microscopically, and its sum expressed by millimeter was taken as an ulcer coefficient of the rat.

The results are shown in Table 20. As is seen in Table 20, the present substance is effective in suppressing the occurrence of stress ulcer, and the amount of 6-keto PGF$_{1\alpha}$ in the plasma was larger in the rats administered with the present substance than in control. Since the raise of the level of 6-keto PGF$_{1\alpha}$, which is a metabolic product of PGI$_2$, means the raise of the level of PGI$_2$, and PGI$_2$ is recognized to be active in suppressing the secretion of stomach juice, and in suppressing the formation of ulcer, it is considered that the present substance exhibits an anti-ulcer function by regulating the level of PGI$_2$.

TABLE 20

| Group | Ulcer-coefficient[1] (%) | Amount of 6-keto PGF$_{1\alpha}$ (ng/ml) |
|---|---|---|
| Stress ulcer and the level of 6-keto PGF$_{1\alpha}$ | | |
| Control | 100 | 3.3 |
| Present substance | | |
| Specimen No. 4 | 62 | 3.8 |
| Specimen No. 7 | 58 | 3.9 |
| Specimen No. 8 | 55 | 3.6 |

Note:
[1]Total sum of the longer spans of erosions on the mucous membrane of the stomach of the treated groups of rat divided by that of control, multiplied by 100.

EXAMPLE 27

Effect of the present substance on pyrexia caused by a pyrogenic bacteria.

The experiments were carried out on cats weighing 3 to 3.5 kg. In an aseptic operation under intraperitoneally administered sodium pentobarbitone at 36 mg/kg, a Collison cannula was implanted into the rostral part of the third ventricle of the cat.

A few days after implantation of the cannula, when the cat had recovered from the operation, specimens of cerebrospinal fluid were collected without anesthesia, whilst the cat was kept unrestrained in its cage, and its rectal temperature was recorded.

The specimens of cerebrospinal fluid (c.s.f.) were assayed immediately after collection, or after having been stored at −2° for 24 to 48 hours, and the determination of PGE in the specimens was carried out as in Example 9 using $^3$H-Prostaglandin E Radioimmunoassay Kit (manufactured by Clinical Assay Co., USA). Rectal temperature was recorded at room temperature (21° to 23° C.) with the thermistor probe inserted about 10 cm deep into the rectum.

As the pyrogen, somatic type o-antigen of *Shigella dysentriae* was used, and after dissolving 75 ng of the pyrogen into 0.15 ml of a pyrogen-free artificial c.s.f., the solution was injected into the third ventricle through the implanted cannula to induce fever.

After 2 hours of administration, the rectal temperature was measured to confirm the occurrence of pyrexia and then the present substance (each of Specimens Nos. 4, 7 and 8) was forcibly administered orally as an aqueous solution in distilled water at a rate of 100 mg/kg, control being administered only with distilled water in this time.

The rectal temperature of all animals was measured after one hour of the administration of the present substance.

The c.s.f. for the determination of its content of PGE was collected respectively before and after 2 hours of the injection of the pyrogen and after one hour of the administration of the present substance.

The results are shown in Table 21.

TABLE 21

| Group | Rectal temperature (° C.) | Amount of PGE (ng/ml of c.s.f.) |
|---|---|---|
| Rectal temperature and amount of PGE in c.s.f. | | |
| Control before admin. pyrogen | 39.0 | 2.5 |
| 2 hours after admin. pyrogen | 41.0 | 12 |
| 1 hour after admin. water* | 40.7 | 10 |
| Administered with the present substance | | |
| Specimen No. 4 | | |
| before admin. pyrogen | 39.0 | 2.6 |
| 2 hours after admin. pyrogen | 41.3 | 11 |
| 1 hour after admin. Specimen | 39.9 | 5 |
| Specimen No. 7 | | |
| before admin. pyrogen | 38.8 | 2.4 |

TABLE 21-continued

| Group | Rectal temperature (°C.) | Amount of PGE (ng/ml of c.s.f.) |
|---|---|---|
| 2 hours after admin. pyrogen | 41.1 | 16 |
| 1 hour after admin. Specimen | 39.5 | 6 |
| Specimen No. 8 | | |
| before admin. pyrogen | 39.1 | 2 5 |
| 2 hours after admin. pyrogen | 41.5 | 13 |
| 1 hour after admin. Specimen | 40.0 | 8 |

Note:
*Distilled water

As is seen in Table 21, the rectal temperature of the cat once raised by the injection of the pyrogen was reduced together with the same tendency of variation of the content of PGE in c.s.f. by the administration of the present substance.

Accordingly, it is considered that the present substance when orally administered to mammal which had a symptom of pyrexia due to the inoculation of a microbial pyrogen exhibits an antipyretic activity presumably in connection to the reduction of PGE in c.s.f.

What is claimed is:

1. A pharmaceutical composition having an activity of regulating production or metabolism of prostaglandins in a mammal in dosage unit form, which comprises a dosage effective to produce said activity of a compound of the formula

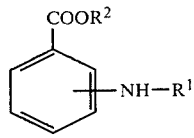

wherein $R^1$ is selected from the group consisting of the residual groups formed by removing OH at 1(alpha)- or 1(beta) position from arabinose, xylose, rhamnose, glucose, galactose, mannose and fructose, and $R^2$ is hydrogen atom or an alkyl of one to four carbon atoms, or a pharmaceutical acceptable salt thereof; and a pharmaceutically acceptable carrier or a diluent therefor.

2. A pharmaceutical composition according to claim 1, wherein said compound is sodium p-aminobenzoate-N-D-mannoside.

3. A pharmaceutical composition according to claim 1, wherein said compound is sodium p-aminobenzoate-N-D-xyloside.

4. A pharmaceutical composition according to claim 1, wherein said compound is sodium p-aminobenzoate-N-D-rhamnoside.

5. A method for regulating the production and metabolism of prostaglandin in a mammal, which comprises administering an effective amount of a compound represented by the general formula:

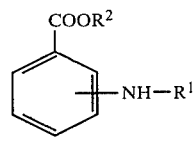

wherein $R^1$ denotes one member selected from the group consisting of the residual groups formed by removing OH at 1(alpha)- or 1(beta) position from arabinose, xylose, rhamnose, glucose, galactose, mannose and fructose, and $R^2$ is a hydrogen atom, an alkyl group of one to four carbon atoms or a pharmaceutically acceptable metal.

6. A method according to claim 5, wherein said compound is sodium p-aminobenzoate-N-D-mannoside.

7. A method according to claim 5, wherein said compound is sodium p-aminobenzoate-N-D-xyloside.

8. A method according to claim 5, wherein said compound is sodium p-aminobenzoate-N-L-rhamnoside.

* * * * *